US010395363B2

(12) United States Patent
Sakimoto

(10) Patent No.: US 10,395,363 B2
(45) Date of Patent: Aug. 27, 2019

(54) IMAGE PROCESSING DEVICE

(71) Applicant: SHIMADZU CORPORATION, Nakagyo-Ku, Kyoto-Shi, Kyoto (JP)

(72) Inventor: Tomonori Sakimoto, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 981 days.

(21) Appl. No.: 14/785,758

(22) PCT Filed: Apr. 25, 2013

(86) PCT No.: PCT/JP2013/002829
§ 371 (c)(1),
(2) Date: Oct. 20, 2015

(87) PCT Pub. No.: WO2014/174553
PCT Pub. Date: Oct. 30, 2014

(65) Prior Publication Data
US 2016/0071262 A1 Mar. 10, 2016

(51) Int. Cl.
*G06T 7/00* (2017.01)
*A61B 6/12* (2006.01)
(Continued)

(52) U.S. Cl.
CPC ............ *G06T 7/0012* (2013.01); *A61B 6/025* (2013.01); *A61B 6/12* (2013.01); *A61B 6/505* (2013.01);
(Continued)

(58) Field of Classification Search
CPC ......... G06T 7/0012; G06T 7/136; G06T 7/12; G06T 7/162; G06T 5/20;
(Continued)

(56) References Cited

U.S. PATENT DOCUMENTS 6,904,163 B1  6/2005  Fujimura et al.
8,908,832 B2  12/2014  Yamashita
(Continued)

FOREIGN PATENT DOCUMENTS

JP  H08140964   6/1996
JP  2001022916  1/2001
(Continued)

OTHER PUBLICATIONS

PCT/JP2013/002829, International Search Report dated Jul. 9, 2013, 5 pages—Japanese, 2 pages—English.
(Continued)

*Primary Examiner* — Peter Luong
(74) *Attorney, Agent, or Firm* — Andrew F. Young; Lackenbach Siegel, LLP

(57) ABSTRACT

According to the image processing device of the present invention, the binarization image having increasing assuredness can be generated by extracting the metal piece from the original image with the graph cut processing. The image processing device of the present invention is the system that executes an image trimming from near the center of the intermediate region after the metal piece is divided relative to the image of the roughly extracted binarization image near the center of the intermediate region in that it is difficult to decide whether it belongs to the metal piece or not. Following such steps, the intermediate region can be assuredly trimmed while executing the image trimming in the region as small as possible.

13 Claims, 30 Drawing Sheets

(51) Int. Cl.
*A61B 6/00* (2006.01)
*A61B 6/02* (2006.01)
*G06T 5/20* (2006.01)
*G06T 7/12* (2017.01)
*G06T 7/162* (2017.01)
*G06T 7/136* (2017.01)

(52) U.S. Cl.
CPC .............. *A61B 6/5252* (2013.01); *G06T 5/20* (2013.01); *G06T 7/12* (2017.01); *G06T 7/136* (2017.01); *G06T 7/162* (2017.01); *G06T 2207/10024* (2013.01); *G06T 2207/10112* (2013.01); *G06T 2207/10116* (2013.01); *G06T 2207/20032* (2013.01); *G06T 2207/30008* (2013.01); *G06T 2207/30052* (2013.01)

(58) Field of Classification Search
CPC ........... G06T 2207/10112; G06T 2207/10024; 06T 2207/10116; G06T 2207/30052; G06T 2207/30008; G06T 2207/20032; A61B 6/025; A61B 6/5252; A61B 6/505; A61B 6/12
See application file for complete search history.

(56) References Cited

U.S. PATENT DOCUMENTS

| | | | |
|---|---|---|---|
| 8,983,029 | B2 | 3/2015 | Hasegawa |
| 9,125,619 | B2 | 9/2015 | Yabugami |
| 2015/0305702 | A1* | 10/2015 | Sakimoto .............. A61B 6/025 |
| | | | 382/131 |

FOREIGN PATENT DOCUMENTS

| | | |
|---|---|---|
| JP | 2007289687 | 11/2007 |
| JP | 2012027696 | 2/2012 |
| WO | WO 2012/164921 | 12/2012 |

OTHER PUBLICATIONS

PCT/JP2013/002829, Written Opinion dated Jun. 28, 2013, 3 pages—Japanese.

Interactive Graph Cuts for Optimal Boundary & Region Segmentation of Objects in N-D Images, Boykov, Jolly, Proceedings of "Internation Conference on Computer Vsion"; Vancouver, Canada, Jul. 2001, vol. 1, pp. 105-112.

* cited by examiner

Median Filter Processing

Binarization Processing

Inside broken line:
Region that can be certainly decided as a metal piece.

FIG. 6(A) 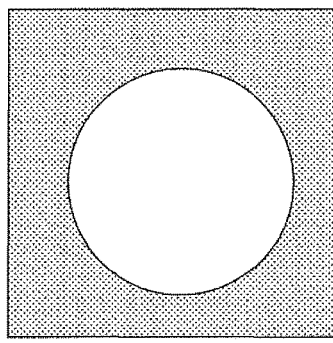 Edge extraction processing FIG. 6(B) 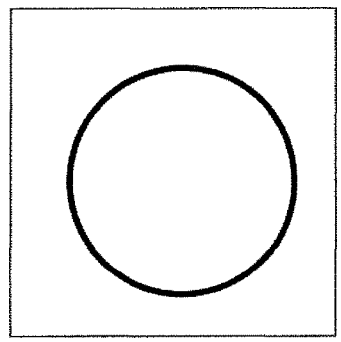

Edge extraction processing

FIG. 10(A)
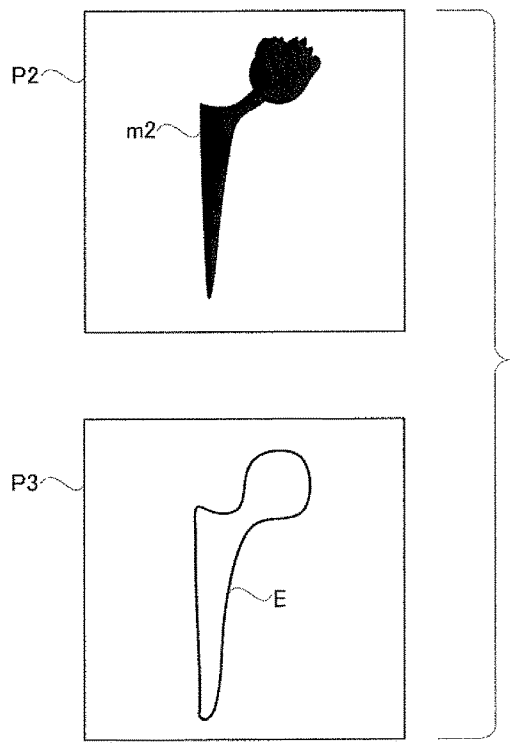
FIG. 10(B)
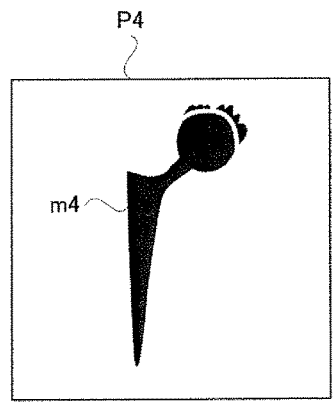
FIG. 10(C)

FIG. 11(A) FIG. 11(B)
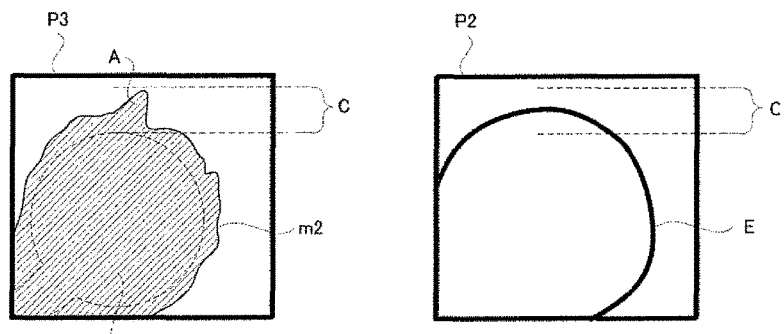
Inside broken line:
Region that can be certainly decided as a metal piece.
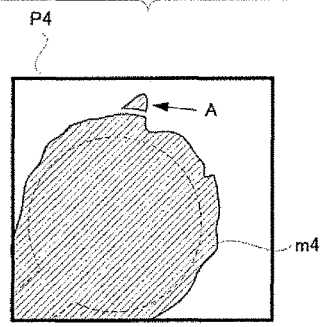
FIG. 11(C)

Profile trimming processing

Trimming

↓ Trimming

Profile trimming processing

FIG. 18(A)     FIG. 18(B)
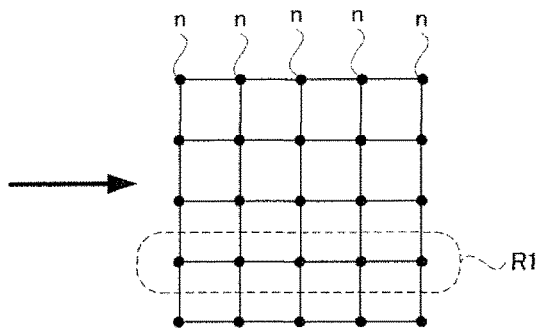

FIG. 19(A)     FIG. 19(B)
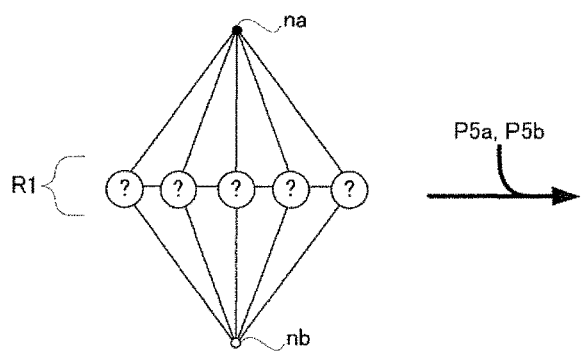

FIG. 21(A)     FIG. 21(B)
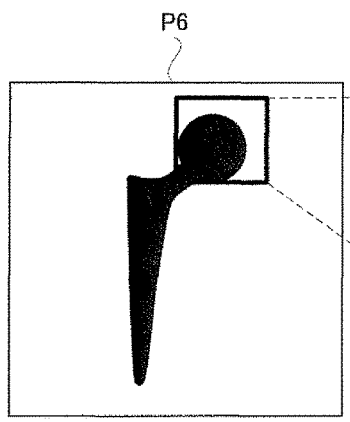
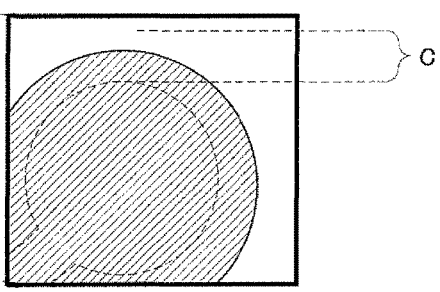

FIG. 22(A)   FIG. 22(B)
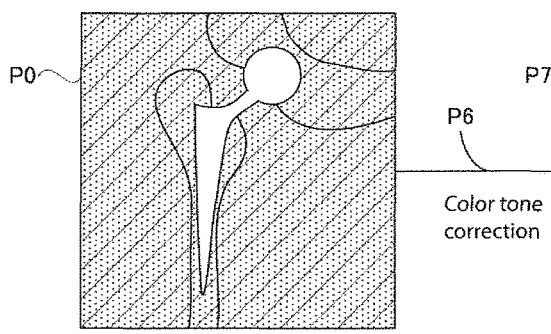
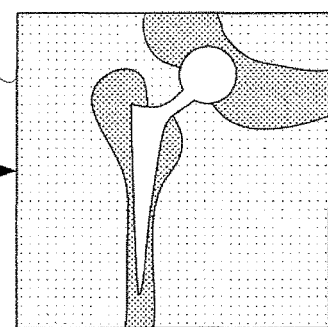
Color tone correction

FIG. 25(A) 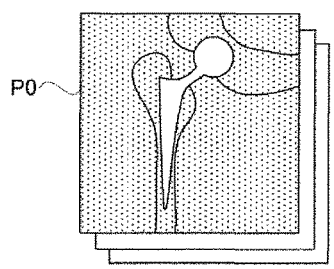 → Extraction processing FIG. 25(B) 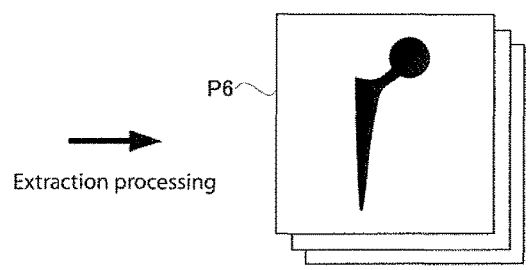

FIG. 26(A)
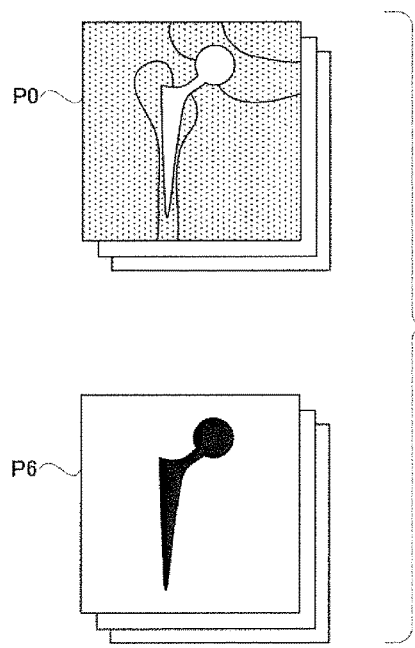
FIG. 26(B)
Metal piece cancel processing
FIG. 26(C)
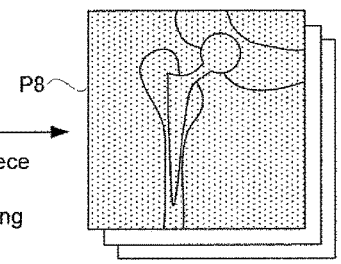

FIG. 28(A)
FIG. 28(B)
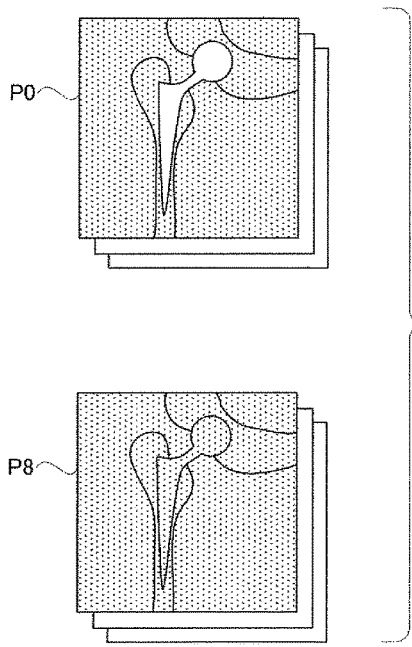
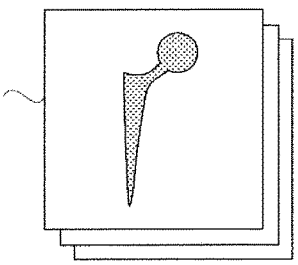
Metal piece trimming processing
FIG. 28(C)

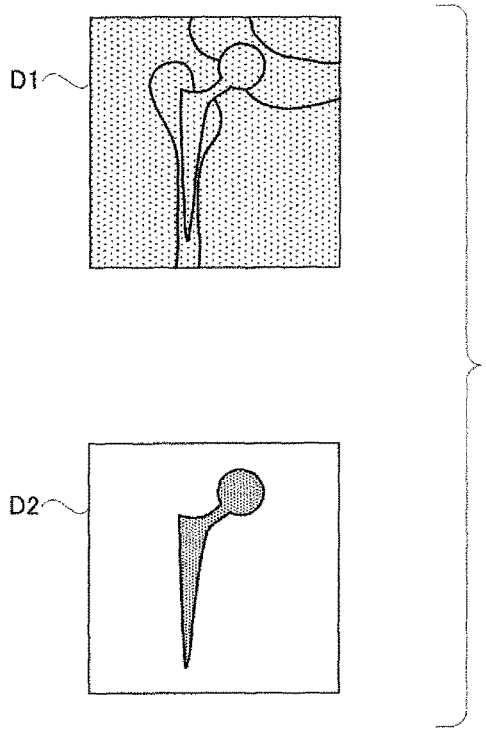
FIG. 30(A)
FIG. 30(B)
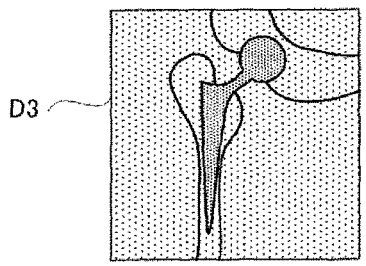
FIG. 30(C)

IMAGE PROCESSING DEVICE

CROSS REFERENCE TO RELATED APPLICATIONS

This reference relates to and claims priority from Ser. No. PCT/JP2013/002829 filed Apr. 25, 2013 the entire contents of which are incorporated herein by reference.

FIGURE SELECTED FOR PUBLICATION

FIG. 1

BACKGROUND OF THE INVENTION

Technical Field

The present invention relates to an image processing device to improve visual recognition of a radiation image, and particularly relates to the image processing device that can provide an image having high visual recognition despite incorporating an image of a metal piece into the radiation image.

Technical Background

A medical facility equips the radiation device to obtain the subject's image using radiation. Such radiographic device comprise the image processing device to display an image having high visual recognition on the monitor by the addition of an image processing on the original image.

The original image prior to image processing is the image as is imaged and the image processing has not been executed yet. Even if the original image as-is displayed on the monitor, the original image having high visual recognition may not be displayed. The image processing device improves the visual recognition of the image incorporated on the monitor by the addition of the image processing on the original image. The image processing device may improve the visual recognition of the image by executing a color tone correction. (Patent Document 1, JP 2007-289687, the entire contents of which are incorporated by reference)

Meantime, in the case of the subject who took a surgery to build up the bone with a metal piece in the past, an image of the metal piece is incorporated into the imaged original image. When the subject having the implanted metal piece inside body is imaged, the hardly radiation transmissive metal piece is obviously incorporated into the original image. The metal piece on the original image appears as an extremely dark image on the original image.

Given the color tone correction is executed without considering the metal piece appeared on the original image, the visual recognition of the image is poorly improved. Because the image processing device improves the visual recognition of the entire image including the extremely dark region of the original image. Therefore, the color tone correction must be performed while excluding the extreme dark region based on the metal piece to assuredly improve the visual recognition of the original image. According to the above method, the color tone correction of the metal piece of the original image would not be executed so that regions other than the metal piece of the original image can be assuredly improved.

Here, as will be noted below, the inventor sets forth the reason why the visual recognition is improved despite color tone correction of only regions other than the metal piece relative to the original image. The metal piece of the original image is not a live tissue of the subject so that it cannot be a focal point of the diagnosis. Specifically, a person in charge of the diagnosis using the image needs to perform a diagnostic imaging of regions other than the metal piece relative to the original image. As set forth above, the color tone correction of regions other than the metal piece relative to the original image is executed so that the visual recognition of the instant regions can be assuredly improved without an impact due to the metal piece relative to the original image. Further, the region subjected to the color tone correction coincides with the regions on which the person in charge of the diagnosis needs to perform the diagnostic imaging. Accordingly, in the case of the original image incorporating the image due to the metal piece, the color tone correction excluding the metal piece can improve further the visual recognition.

First, as set forth above, it must be understood which region of the original image should be assigned as the image due to the metal piece so as to perform the color tone correction excluding the metal piece. The assignment is provided prior to the color tone correction. A graph cut method is applied at this time. The graph cut method is the method to decide whether the instant image of the original image is due to the metal piece or not by considering the brightness of pixels per se constituting the image and the difference of the pixels between the instant pixel and the adjacent pixel thereto.

According to the graph cut method, brightness of the metal piece of the original image must be specified prior to the operation. A region of the metal piece of the original image can be selected to accomplish the specification therefor at this step. The selection requires exactitude. If the selected region includes any non-metal piece region, the aspect recognition of the metal piece based on the graph cut method would be inaccurate so that the bottom-line visual recognition of the image obtained by the color tone correction can be adversely impacted.

A conventional method is utilizing a binarization processing of the image to specify brightness of the metal piece of the original image as set forth above. The metal piece on the original image is extremely dark in the image. Accordingly, the binarization processing is executed so as to let the dark region of the original image come up so that an assignment of the metal piece can be performed.

As set forth above, the case in which the color tone correction is executed relative to the original image is illustrated as an example, the binarization processing is being utilized for an image processing other than the color tone correction. For example, the binarization processing is utilized to prevent that the false image appears in the periphery of metal piece incorporated into the tomographic image formed by executing the image reconstruction processing on the original image continuously imaged while changing the imaging position of the subject. (Patent Document 2, Ser. No. PCT/JP2012/003525)

PRIOR ART DOCUMENTS

Patent Document

Patent Document 1: JP Patent Published 2007-289687

Patent Document 2: PCT/JP2012/003525

[Non Patent Document 1]

Yuri Y. Boykov, Marie-Pierre Jolly; Interactive Graph Cuts for Optimal Boundary & Region Segmentation of Objects in N-D Images. Proceedings of "International Conference on Computer Vision", July 2001 vol. 1, p. 105)

ASPECTS AND SUMMARY OF THE INVENTION

Problems to be Solved by the Invention

However, there are following problems in the conventional constitution. Specifically, the binarization processing having the conventional constitution provides an inaccurate assignment of the metal piece.

According to the conventional method, the shape of the metal piece relative to the entirety of original image is recognized by firstly extracting the dark region of the original image. The first half of the processing is the binarization processing of the image and the second half of processing is the graph cut operation. The binarization processing is performed based on comparison of the pixel value of pixels constituting the original image and the predetermined threshold value. Accordingly, the pixel due to a region other than the metal piece of the original image may be erroneously recognized as in-place in the metal piece depending on the threshold value. Once this kind of erroneous recognition takes place, the following graph cut operation would never correct the error. Accordingly, at the time when the binarization processing is executed, the occurrence of the above erroneous recognition must be assuredly prevented.

However, it is difficult to avoid the above erroneous recognition by only conventional binarization processing. In some cases, more radiation absorptive cement is in-place in the periphery of the metal piece of the subject so that discrimination of the cement and the metal piece incorporated into the original image may be difficult when the binarization processing is performed.

Accordingly, when the binarization processing is performed, it is difficult to select an optimal threshold value suitable for each of the original image. So, according to the conventional constitution, it is constituted as the same binarization processing is executed relative to the different original image. Following such fact, the conventional method for the binarization processing will include non-metal piece region in the metal piece region when the metal piece is extracted from the original image. This causes an erroneous recognition of the metal piece on the original image so that the color tone correction and the cross section image generation processing executed relative to the original image can be adversely impacted.

Under such circumstance, the present invention is completed and the purpose thereof is to provide an image processing device that can assuredly improve the visual recognition relative to a region other than a metal piece incorporated into the image by accurately discriminating the metal piece and other region's image relative to the image incorporating the metal piece.

Means for Solving the Problem

The present invention comprises the following system to solve the above problem.

Specifically, an image processing device of the present invention is the image processing device that executes an image processing on an original image incorporating a metal piece obtained by the radiation imaging of the subject having an implanted metal piece inside comprises: a binarization means that generates a binarization image incorporating a rough metal piece incorporated into the original image by binarization of the original image; an edge extraction processing means that generates an edge extraction image, wherein the boundary indicating the position near the center of the intermediate region between the region exposed more to radiation and the region exposed less thereto relative to the original image is extracted by the edge extraction processing on the original image; an image synthesis means that generates a synthetic image, wherein an image on the binarization image is divided near the center region of the intermediate region by superimposing the binarization image and the edge extraction image; a profile trimming means that generates a profile trimming map, wherein the intermediate region is trimmed from the image on the synthetic image by trimming the profile of the image on the synthetic image; and a graph cut means that generates an extraction image, wherein the metal piece incorporated into the original image is extracted by executing a graph cut processing relative to the original image while recognizing that the image on the profile trimming metal map constitutes a region of the metal piece incorporated into the original image.

[Action and Effect]According to the image processing device of the present invention, the accurate binarization image can be generated. Specifically, the image processing device of the present invention decides by executing a graph cut processing whether the intermediate region between the region exposed more to radiation and the region exposed less thereto relative to the original image is belonging to the metal piece or not. Accordingly, the profile of the metal piece incorporated into the original image can be exactly extracted. Specifically, the image processing device of the present invention comprises; the binarization means that generates the binarization image incorporating a rough metal piece incorporated into the original image by binarization of the original image, the edge extraction processing means that extracts the position near the center of the intermediate region of the original image, the image synthesis means that generates a synthetic image that is divided near the center region of the intermediate region, the profile trimming processing means that removes the intermediate region by trimming the profile of the image on the synthetic image. Accordingly, the inside aspect of the metal piece incorporated into the original image can be exactly extracted.

Further, the above image processing device preferably comprises: a median filer processing means that perform a median filter relative to the original image; and wherein further preferably the original image to which the binarization processing means, the edge extraction means and the graph cut processing means are referring is executed by the median filter.

[Action and Effect]The above system illustrates further specifically an image processing device of the present invention. If the original image to which the binarization processing means, the edge extraction means and the graph cut processing means are referring is executed by the median filter, the noise component appeared in the original image is trimmed by the median filer so that the metal piece incorporated in the original image can be more exactly extracted.

Further, the above image processing device preferably comprises the edge extraction processing means is further preferably operative to execute Laplacian filter to the original image.

[Action and Effect]The above system illustrates further specifically an image processing device of the present invention. The edge extraction processing means can extract assuredly near the center of the intermediate region by executing Laplacian filter to the original image. Because Laplacian filter is a spacial differential filter.

Further, the above image processing device preferably comprises: an inversion means that generates an inversion-binarization image incorporating a rough image regions other than the metal piece incorporated into the original image by executing the image processing relative to the binarization image; an image synthesis means that generates a synthetic image relative to the inversion, wherein an image on the inversion-binarization image is divided near the center region of the intermediate region by superimposing the inversion-binarization image and the edge extraction image; a profile trimming means that generates a profile trimming metal map, wherein the intermediate region is trimmed from the image on the synthetic image by trimming the profile of the image on the synthetic image relative to the inversion; and it will be further preferred that a graph cut means executes a graph cut processing relative to the original image while recognizing as the image on the profile trimming metal map constitutes a region of regions other than the metal piece incorporated into the original image.

[Action and Effect]The above system illustrates the operation of regions other than the metal piece on the original image. Specifically, the image processing device of the present invention generates the inversion-binarization image incorporating a rough image of regions other than metal piece incorporated into the original image and generates a synthetic image relative to inversion, wherein an image on the inversion-binarization image is divided near the center region of the intermediate region; and then after, the system trims the intermediate region from the image on the synthetic image by trimming the profile of the image on the synthetic image.

Accordingly, the inside aspect of the metal piece incorporated into the original image can be exactly extracted by each means. Specifically, based on these means, the assignment of the region other than metal erroneously detected as the metal relative to the metal boundary region can be canceled.

Further, it will be further preferred that the above image processing device comprises a color tone correction processing means to execute the color tone correction processing for the region other than the metal piece relative to the original image referring to the extraction image.

[Action and Effect]The image processing device of the present invention can be used for the color tone correction.

Further it will be preferred that the image processing device comprises a metal piece cancel processing that generates a metal piece cancel g image referring to the extraction image, wherein the metal piece is extracted from each original image continuously imaged while changing the imaging direction relative to the subject, a metal piece cancel tomographic image generation processing that generates metal piece cancel tomographic image by executing an image reconstruction processing on a plurality of the metal piece cancel image, a metal piece trimming processing that generates a trimming image by taking out the corresponding regions to the metal piece from the each original image referring to the extraction image, a metal piece tomographic image generation processing that generates metal piece tomographic image by executing an image reconstruction processing on a plurality of the trimming images, and a tomographic image generation means that executes the tomographic image adding processing so as to generate the synthetic tomographic image by adding the metal piece cancel tomographic image and the metal piece tomographic image.

[Action and Effect]

The image processing device of the present invention can be used for the case of generation of the tomographic image without occurrence of a false image in the periphery of the metal piece.

Effects of the Invention

[Action and Effect]According to the image processing device of the present invention, the binarization image having increasing assuredness can be generated by extracting the metal piece from the original image with the graph cut processing. The image processing device of the present invention is the system that executes an image trimming from near the center of the intermediate region after the metal piece is divided relative to the image of the roughly extracted binarization image near the center of the intermediate region in that it is difficult to decide whether it belongs to the metal piece or not. Following such steps, the intermediate region can be assuredly trimmed while executing the image trimming in the region as small as possible.

The above and other aspects, features and advantages of the present invention will become apparent from the following description read in conjunction with the accompanying drawings, in which like reference numerals designate the same elements.

BRIEF DESCRIPTION OF THE DRAWINGS

FIGS. 6(A) and 6(B) are schematic diagrams illustrating an edge extraction processing of Embodiment 1.

FIGS. 10(A), 10(B), and 10(C) are schematic diagrams illustrating an image synthesis processing of Embodiment 1.

FIGS. 11(A), 11(B) and 11(C) are schematic diagrams illustrating an image synthesis processing of Embodiment 1.

FIGS. 18(A) and 18(B) are schematic diagrams illustrating a graph cut processing of Embodiment 1.

FIGS. 19(A) and 19(B) are schematic diagrams illustrating a graph cut processing of Embodiment 1.

FIGS. 21(A) and 21(B) are schematic diagrams illustrating a graph cut processing of Embodiment 1.

FIGS. 22(A) and 22(B) are schematic diagrams illustrating a color tone correction processing of Embodiment 1.

FIGS. 25(A) and 25(B) are schematic diagrams illustrating an acquisition operation of the tomographic image of Embodiment 2.

FIGS. 26(A), 26(B), and 26(C) are schematic diagrams illustrating an acquisition operation of the tomographic image of Embodiment 2.

FIGS. 28(A), 28(B) and 28(C) are schematic diagrams illustrating an acquisition operation of the tomographic image of Embodiment 2.

FIGS. 30(A), 30(B), and 30(C) are schematic diagrams illustrating an acquisition operation of the tomographic image of Embodiment 2.

DETAILED DESCRIPTION OF PREFERRED EMBODIMENTS

The image processing device of the present invention is an image processing device that executes an image processing on an original image P0 incorporating a metal piece obtained by radiation imaging of the subject having an implanted metal piece inside. Hereafter, the inventor illustrates the best mode of Embodiment of the present invention.
Embodiment 1

Figure 1:
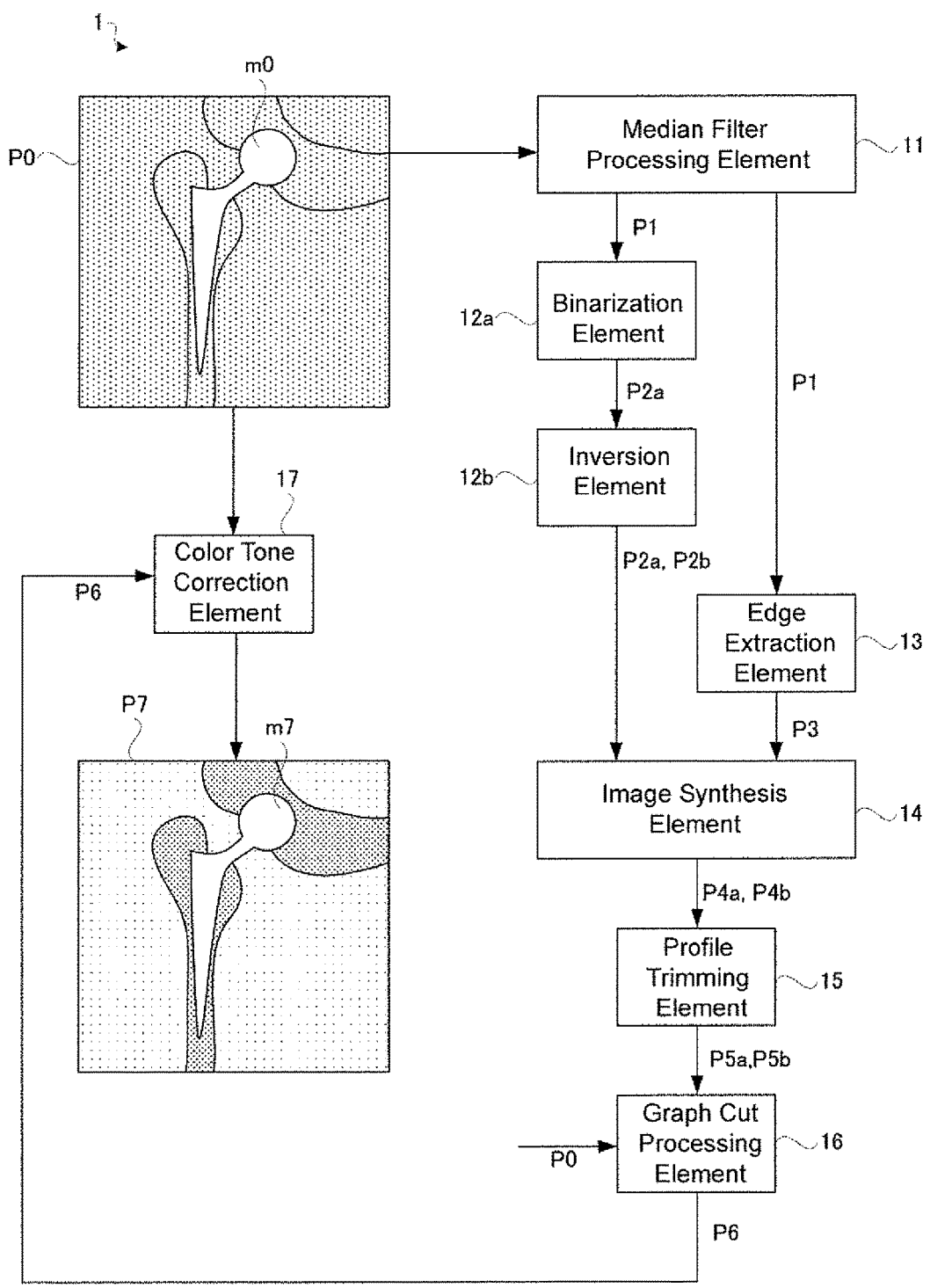
FIG. 1 is a functional block diagram illustrating the total system of the image processing device of Embodiment 1.

First, the inventor sets forth Embodiment of the image processing device 1. Referring to FIG. 1, the system of the image processing device of the present invention outputs a color tone correction image P7 that is generated by the color tone correction of the original image P0 when the original image P0 is input. The original image P0 can be a variety of images, but it is given that the original image P0 is the image obtained by the X-ray radiography of the subject having an implant metal piece for the purpose of representing most effectively the characteristics of the present invention. And it is given that an image of the metal piece inside the subject is incorporated into the original image P0. Specifically, the original image P0 in FIG. 1 illustrates the metal piece m0 constituting an artificial joint. Further, it is given that the regions other than the metal piece m0 in the original image P0 are constituted from pixels having a similar pixel value so that the high visual recognition cannot be provided.

When such original image P0 is input into the image processing device 1 of Embodiment 1, the color tone correction is executed on the original image P0. Accordingly, the pixel value of pixels constituting the original image P0 would take a predetermined adjustment and is converted to the color tone correction image P7 having improved visual recognition. At this time the image processing device 1 is characterized in that the color tone correction is not being applied to all regions of the original image P0. Specifically, the image processing device 1 executes the image processing only on the regions than the metal piece m0 excluding the metal piece m0 incorporated into the original image P0. Accordingly, the metal piece m0 incorporated into the original image P0 is as if copied onto the color tone correction image P7 from the original image P0 without receiving image processing.

The visual recognition of the color tone correction image P7 other than the metal piece m7 is deemed improved for a person in charge of diagnosis. Specifically, the metal piece m0 incorporated into the original image P0 is not live tissues of the subject so that the other region of the original image P0 than the metal piece m0 can be more of interest for the person in charge of diagnosis. Such regions comprise pixels having a similar pixel value relative to the original image P0 so that the visual recognition can be low because of unclear components. However, contrast of the pixel value of the regions is adjusted relative to the color tone correction image P7 so that the visual recognition can be improved. Accordingly, the person in charge of diagnosis can provide an accurate diagnosis as to the other regions of the metal piece m0 of which visual recognition is improved by using the diagnosis of the color tone correction image P7.

The image processing device 1 is structurally operative so as to correct the color tone relative to the original image P0 excluding the metal piece m0b because it is required to assuredly improve the visual recognition of other regions than the metal piece m0 If the image processing device 1 executes the color tone correction of the original image P0 including the metal piece m0, regions other than metal piece m0 on the original image P0 look darker overall because of impact of the pixel value of the metal piece m0 incorporated as extremely whity on the original image P0 so that the visual recognition of regions other than the metal piece m0 cannot be very improved. Then, the image processing device of Embodiment 1 is operative to correct the color tone of regions other than the metal piece m0 by recognizing the aspect of the metal piece m0 incorporated into the original image P0 prior to the color tone correction.

The image processing device 1 comprises each element 11, 12, 12a, 13, 14, 15, 16 in order to extract the metal piece m0 from the original image P0. Among them, the median filter processing element 11 generates the filter processing image P1 by executing the median filter to the original image P0. The binarization element 12a generates the binarization image P2a by executing the binarization processing to the filter processing image P1. The inversion element 12b generates the inversion binarization image P2b by inversion of the binarization image P2a. The edge extraction element 13 generates the edge extraction image P3 by executing an extraction processing to the filter processing image P1. The image synthesis element 14 superimposes the binarization image P2a and the edge extraction image P3 to generates the synthetic image P4a and superimposes the inversion binarization image P2b and the edge extraction image P3 to generates the synthetic image P4b relative to the inversion. The profile trimming element 15 generates the profile trimming metal map P5a by executing the profile trimming processing to the synthetic image P4a and generates the profile trimming non-metal map P5b by executing the profile trimming processing to the synthetic image P4b relative to the inversion. The graph cut processing element 16 generates the extraction image P6a; wherein the metal piece m0 is extracted from the original image P0 based on the original image P0, the profile trimming metal map P5a and the profile trimming non-metal map P5b.

Accordingly, the median filter processing element 11 corresponds to the median filter processing means of the present invention and the binarization element 12a corresponds to the binarization means of the present invention and the inversion element 12*b* corresponds to the inversion means of the present invention. Further, the edge extraction element 13 corresponds to the edge extraction processing means of the present invention and the image synthesis element 14 corresponds to the image synthesis means of the present invention. Further, the profile trimming element 15 corresponds to the profile trimming processing means of the present invention and the graph cut processing element corresponds to the graph cut processing means of the present invention.

Then, the image processing device 1 generates the color tone correction image P7 by recognizing the position/size/region of the metal piece m0 on the original image P0 based on the extraction image P6 and by executing the color tone correction as for regions other than the metal piece m0 on the original image P0. The color tone correction element 17 executes such color tone correction. Hereafter, the inventor sets forth the specific operation of each element in order. The color tone correction element 17 corresponds to the color tone correction processing means of the present invention.

Operation of Median Filter Element 11

Figure 2A:
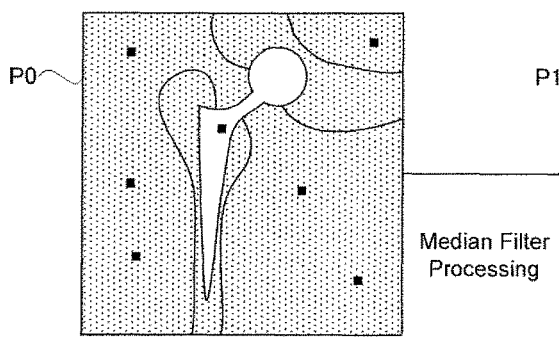
FIGS. 2(A) and 2(B) are schematic diagrams illustrating a median filter processing of Embodiment 1.
Figure 2B:
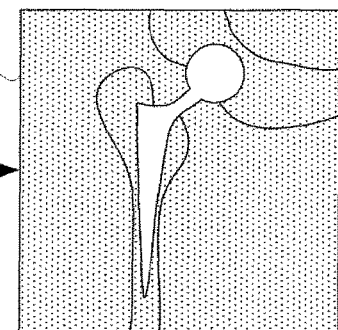

FIG. 2(A)(B) is illustrating the filter processing of the median filter processing element 11 relative to the original image P0. The original image P0 includes fine particle like noise shown in FIG. 2(A). Such noise is either extremely dark or extremely bright relative to the original image P0. Such noise disturbs the extraction of metal piece m0 being executed. Then, according to the present invention, the median filter processing element 11 erases the particle like noise on the original image P0 prior to the extraction operation. Specifically, the noise erase can be performed by that the median filter processing element executes the median filter relative to the original image P0. The image generated by this processing is called as a filter processing image P1.

The median filter processing is a kind of matrix filter used in the image processing, wherein the image processing replaces the pixel value of pixels constituting the image by the pixel in the periphery of the pixel thereof. Accordingly, the pixel value of pixels is replaced by the intermediate pixel value among the pixel values of the peripheral pixels. According to this operation, the noise appeared in the original image P0 can be trimmed. Accordingly, the median filter processing element 11 executes the median filter relative to the original image P0. The filter image that the binarization element, the edge extraction means and the graph cut processing element 16 as set forth later are referring is executed by the median filter.

Operation of the Binarization Element 12*a*

The filter processing image P1 is sent out to the binarization element 12*a*. The binarization element 12*a* temporarily extracts the metal piece m0 on the original image P0 based on the pre-set threshold value. Specifically, the binarization element 12*a* decides whether the instant pixel belongs to more radiation exposed region or less exposed region by comparing the pixel value of pixels constituting the original image P0 and the threshold value. The binarization element 12*a* performs the decision relative to all pixels on the original image P0 and, referring to FIG. 3(B), and outputs the decision results as the binarization image P2*a*. In the case of FIG. 3(B), the black region is decided as less radiation exposure. In the case of FIG. 3, the white region is decided as more radiation exposure. The pixel value of pixels of the black region of the binarization image P2*a* is 1 and the pixel value of the white region is 0. Accordingly, the binarization element 12*a* generates a binarization image p2*a* incorporating a rough image of the metal piece m0 incorporated into the original image P0 by binarization of the original image P0.

In addition, the inversion element 12*b* generates the inversion binarization image P2*b* by inversion of the binarization image P2*a*. The inversion binarization image P2*b* is the one that is set forth later. The inversion element 12*b* generates an inversion-binarization image P2*b* incorporating a rough image of regions other than the metal piece m0 incorporated into the original image P0 by executing the inversion processing relative to the binarization image P2*a*, Accordingly, the obtained binarization image P2*a* represents roughly the position of the metal piece m0 relative to the original image P0. A metal can characteristically and extremely absorb X-ray compared to e.g., bone that builds the subject. Accordingly, the metal piece m0 relative to the original image P0 is extremely less exposed to X-ray. And the original image P0 is a photograph obtained by exposing to X-ray. Accordingly, if pixels of the original image P0 are divided into two groups based on the size of the pixel value, the group of pixels grouped as less radiation exposure should constitute the metal piece m0 having extremely less exposure to X-ray.

Figures 4A, 4B:
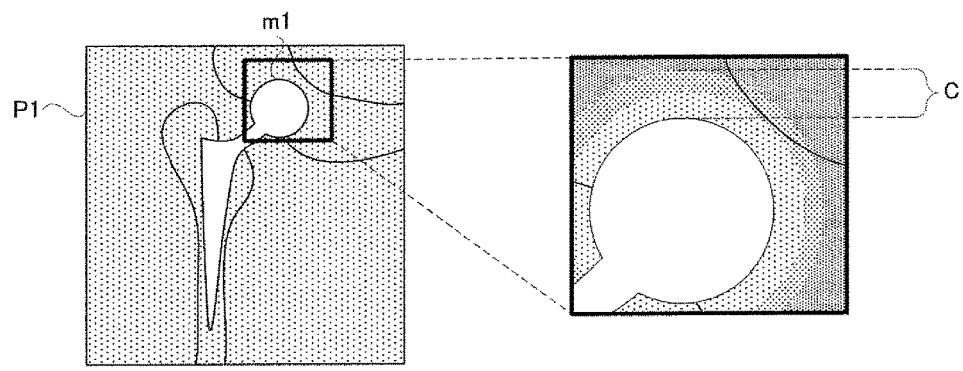
FIGS. 4(A) and 4(B) are schematic diagrams illustrating an intermediate region of Embodiment 1.

However, the binarization processing cannot provide an exact aspect of the metal piece m0. FIG. 4(A)(B) are illustrating the rationale therefor. Referring to the expanded region of the filter processing image P1, it is found that a graduation appears between the metal piece m1 of the filter processing image P1 and other regions. Specifically, the intermediate region C that is difficult to be assigned to either region at first glance exists between the metal piece m1 of the filter processing image P1 and other regions. Many pixels having the similar pixel value to the pixel value given by the above threshold value are found in the intermediate region C. Accordingly, the binarization processing is executed relative to the intermediate region C, an erroneous recognition of the decision as to whether the pixel belongs to the metal piece m1 or not takes place.

Referring FIG. 3(B), it will be understood that the aspect of the metal piece m2 on the binarization image P2*a* and the aspect of the metal piece m1 on the filter processing image P1 are different each other. As set forth above, the aspect of the metal piece m2 on the binarization image P2*a* is disturbed by the erroneous recognition of the decision found relative to the intermediate region C.

Figure 5:
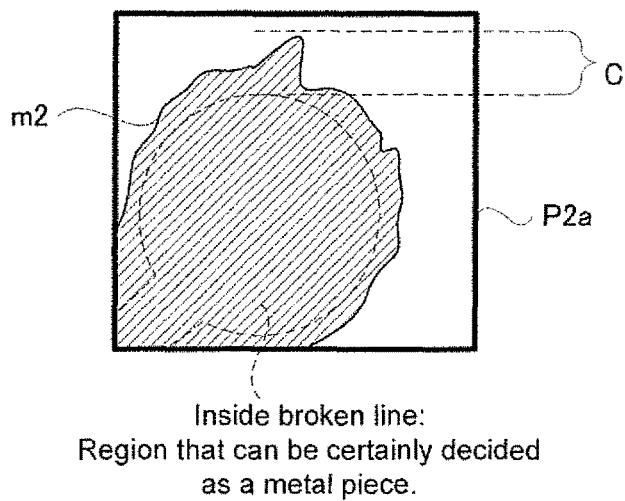
FIG. 5 is a schematic diagram illustrating a binarization processing of Embodiment 1.

FIG. 5 is a partial expanded diagram of the binarization image P2*a* illustrating such aspect. The metal piece m2 on the binarization image P2*a* sticks out to the intermediate region C covering the region obviously due to the metal piece inside broken lines. Accordingly, the boundary of the aspect of the metal piece m2 on the binarization image P2*a* is inaccurate. Accordingly, the other method than the binarization processing so as to accurately recognize the metal piece in the intermediate region at which it is difficult to make a decision as to whether it is subject to such certain metal piece or not. However, relative to the binarization image P2*a*, the boundary between the metal piece and regions other than the metal piece has been decided inaccurately based on the independent criterion. Then, the region corresponding to the intermediate region C relative to the binarization image P2*a* is firstly trimmed from the metal piece m2 and then, it is required to perform a detail analysis whether the trimmed region is a metal piece or not by using more assured method. Firstly the aspect of the intermediate region C must be understood to execute such operation.

Operation of the Edge Extraction Element 13

The edge extraction element 13 is installed in order to extract the above intermediate region C from the filter processing image P1. FIG. 6(A)(B) are illustrating about what the edge extraction processing that is performed on the filter processing image P1 by the edge extraction element 13 is. First, referring to FIG. 6(A), it is given that an image having the bright circle image incorporated into the dark image. As illustrated in FIG. 6(B), if the edge extraction is performed, the circle region and the region other than the circle are obtained in different colors. In addition, the image generated by the edge extraction processing is not a binarization image, but the image is illustrated as a binarization image for convenience of illustration in FIG. 6(A)(B). The edge extraction processing is performed by executing Laplacian filter processing on the image. Laplacian filter processing is a kind of image processing to enable enhancing the boundary between the image incorporated into the image and the background thereof by a differential processing.

Figure 7A:
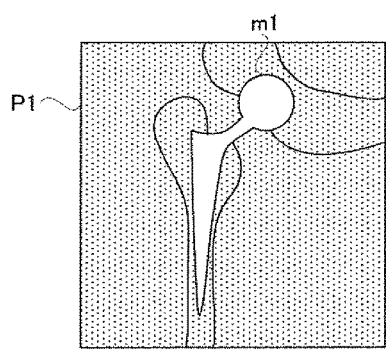
FIGS. 7(A) and 7(B) are schematic diagrams illustrating an edge extraction processing of Embodiment 1.

FIG. 7(A)(B) are illustrating the operation by which the edge extraction element 13 generates the edge extraction image P3 by executing an edge extraction processing on the filter processing image P1. At this time, the edge extraction image P3 is an extracted image of the boundary between the metal piece m1 of the filter processing image P1 and the background (regions other than the metal piece m1).

Figure 3A:
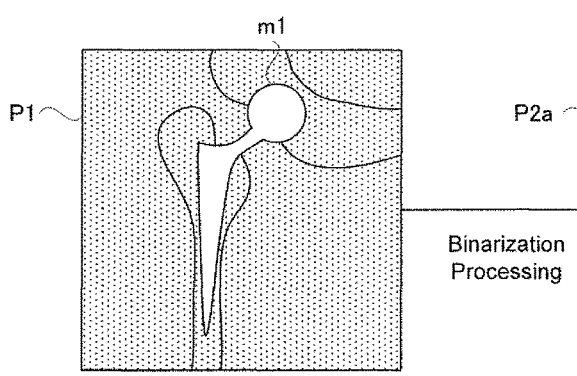
FIGS. 3(A) and 3(B) are schematic diagrams illustrating a binarization processing of Embodiment 1.
Figure 3B:
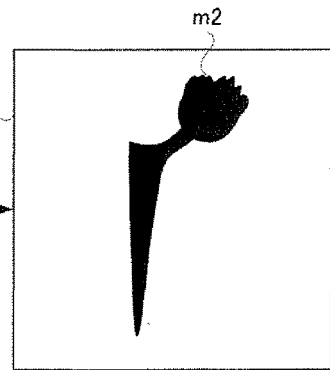
Figure 7B:
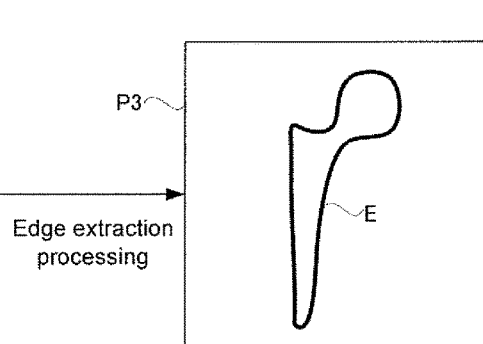
Figure 8A:
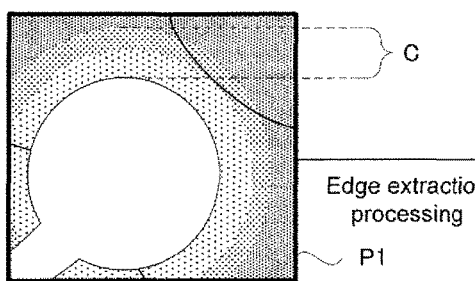
FIGS. 8(A) and 8(B) are schematic diagrams illustrating an edge extraction processing of Embodiment 1.
Figure 8B:
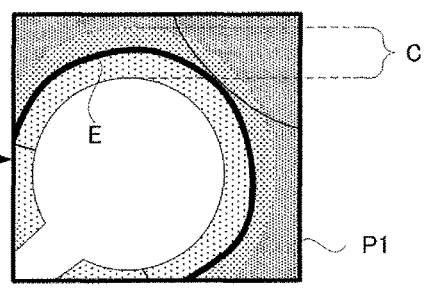

Here, it is noticed that if the metal piece m1 of the filter processing image P1 in FIG. 3(A) and the edge E of the edge extraction image P3 in FIG. 7(B), looking like a ring, are compared, each aspect is somewhat different. FIG. 8(A)(B) are illustrating the rationale why such phenomenon takes place. FIG. 8(A) is an expanded view of the region of the filter processing image P1. As set forth referring to FIG. 4(B), the intermediate region C between the metal piece incorporated into the filter processing image P1 and regions other than the metal piece cannot be discriminated by the binarization processing as to which region should be assigned. FIG. 8(B) is illustrating the edge E obtained by executing an edge extraction processing on the filter processing image P1 illustrated in FIG. 8(A). FIG. 8(B) depicts a superimposition of two of the Edge E and the filter processing image P1 that is a base of the edge extraction processing. The edge E is in place near the center of the intermediate region C in light of the property of the image processing.

Figure 9:
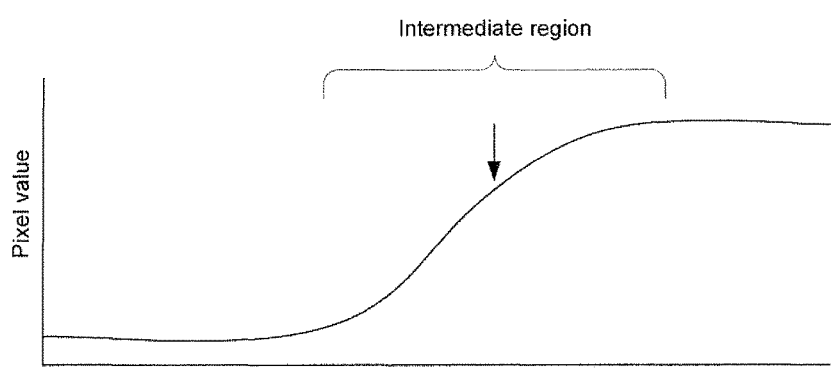
FIG. 9 is a schematic diagram illustrating an edge extraction processing of Embodiment 1.

FIG. 9 is illustrating the rationale why the intermediate region is in place near the center of the intermediate region C. The graph in FIG. 9 is a graph illustrating the relationship between the pixel value and the position on the filter processing image P1. The left side of the graph corresponds to the region in which regions other than the metal piece m1 on the filter processing image P1 is incorporated and the right side of the graph corresponds to the region in which the metal piece m1 on the filter processing image P1 is incorporated. The intermediate between each region is the intermediate region C. Here, the inventor sets forth where the edge extraction would appear in the graph of FIG. 9 if the edge extraction processing is executed on the filter processing image P1. The edge extraction by the edge extraction element 13 is performed by spatially differentiating pixels. That is, the edge E will appear in the region having the biggest slope when the graph is differentiated. With the above fact in mind, the graph of FIG. 9 is carefully reviewed once more. Reviewing the graph from left to right, the state with fairly constant pixel value gradually changes to which the pixel value is growing largely and then the growth of the pixel value declines and in which the pixel value is almost stationary. Because the change corresponding to the position of the pixel value on the X-ray image is qualitatively moderate and not suddenly. That is, relative to FIG. 9, the edge E appears near the center of the intermediate region C indicated by the arrow, at which the growth of the pixel value is the highest.

Accordingly, an edge extraction element 13 generates an edge extraction image P3, wherein the edge E indicating the position near the center of the intermediate region C between the regions exposed more to radiation and the regions exposed less thereto relative to the original image P0 is extracted by executing the edge extraction processing on the original image P0. Accordingly, relative to the binarization image P2a, the operation to trim the region (stick-out region: outside of the broken lines in FIG. 5), in which the metal piece m2 is sticking out to the intermediate region C, from the binarization image P2a can be executable.

Operation of the Image Synthesis Element 14

The binarization image P2a and the edge extraction image P3 are sent to the image synthesis element 14. The image synthesis element 14 replaces the pixel value of the binarization image P2a to zero, in which the edge extraction image P3 superimposes the edge E by superimposing the binarization image P2a and the edge extraction image P3. FIG. 10(A)(B)(C) are illustrating the operation thereon. The metal piece m4 that is the same as the metal piece m2 on the binarization image P2a at the first glance is incorporated into the synthetic image P4a obtained as set forth above but these are different each other at the second glance. Specifically, the metal piece m2 appears as one lump on the image but in contrast, the metal piece m4 has a variety of cuts due to the edge E. Accordingly, the metal piece m4 is divided into a plurality of regions. The image synthesis element 14 generates a synthetic image P4a, wherein the image on the binarization image P2a is divided near the center region of the intermediate region by superimposing the binarization image P2a and the edge extraction image.

FIG. 11(A)(B)(C) is illustrating which regions of the metal piece m2 on the binarization image P2a have cuts due to the image synthesis processing based on the expanded region of each image. The metal piece m2 sticks out to the intermediate region C and the edge E is in place in the center of the intermediate region C so that no cut can be clearly found in the region belonging to the metal piece (i.e. the region out of the intermediate region C) in the metal piece m4 relative to the synthetic image P4a. Rather, some cuts relative to the metal piece m4 can be found in the protruding region as illustrated as A in FIG. 11(A). Relative to the metal piece m2, the protruding region is the large stick-out region that covers almost all over the intermediate region C crossing the center of the intermediate region C. The pixel value of pixels in-place in the center of the intermediate region C on the binarization image P2a is converted to zero in the image synthesis processing so that the protruding region can be isolated from the metal piece on the image by the channel occurred by the conversion of the pixel value. Accordingly, the region A relative to the metal piece m4 in FIG. 11(C) is represented as if a solitary island. Accordingly, pixels in-place near the center of intermediate region C relative to the metal piece P2a can be trimmed from the metal piece by the image synthesis processing. However, it will be understood that all stick-out regions (outside of the broken line) depicted in FIG. 11(C) in the certain image processing.

Operation of Profile Trimming Element 15: Generation of the Profile Trimming Metal Map 5a The purpose of the profile trimming element 15 is to convert the residual pixel value of the stick-out region relative to the synthetic image P4*a* to zero. Accordingly, all stick-out regions of the metal piece m2 on the binarization image P2*a*, which are sticking out to the intermediate region C, will be trimmed from the metal piece m2. Accordingly, the profile trimming element 15 that generates a profile trimming metal map P5*a*, wherein the intermediate region C is trimmed from the image on the synthetic image P4*a* by trimming the profile of the image on the synthetic image P4*a*.

The inventor sets forth the image processing actually executed by the profile trimming element 15. The profile trimming element 15 trims only the predetermined width of the metal piece m4 on the synthetic image P4*a*. Trimming executed by the profile trimming element 15 is the operation by which the pixel value of pixels constituting the profile thereof is changed to zero relative to the lump of pixels incorporated in the image and it is different mode from general shrinking of figures.

Figure 12A:
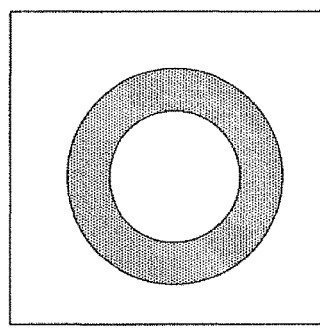
FIGS. 12(A) and 12(B) are schematic diagrams illustrating a profile trimming processing of Embodiment 1.
Figure 12B:
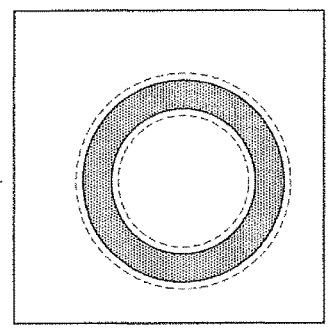

FIG. 12(A)(B) are illustrating the profile trimming processing executed by the profile trimming element 15. For example, it is given that an image incorporating the circle shape image as shown in FIG. 11(A). If the profile trimming processing is executed on the image, the profile region of the circle shape image is trimmed; the circle could be narrow as illustrated in FIG. 11(B). The broken line region in FIG. 11(B) is illustrating the profile of the image prior to trimming.

Figure 13A:
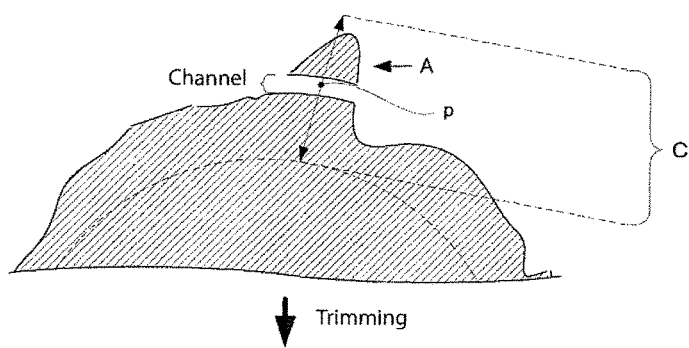
FIGS. 13(A) and 13(B) are schematic diagrams illustrating a profile trimming processing of Embodiment 1.
Figure 13B:
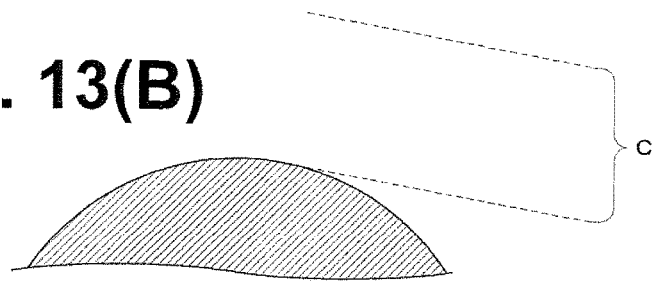

FIGS. 13(A)(B) are specifically illustrating the profile trimming processing performed by the profile trimming element 15 on the synthetic image P4*a*. The profile trimming element 15 continues the trimming operation for a lump of pixels constituting the metal piece m4 from the profile thereof until all pixels belonging to the intermediate region C (pixels belonging to the stick-out region) are trimmed. Accordingly, the width of the intermediate region C must be acquired in advance prior to the image processing. The width of the intermediate region C can be easily acquired by observing the original image P0. Further, once the width of the intermediate region C is acquired, the acquired width can be used for the profile trimming processing relative to other X-ray image. Because the width of the intermediate region C might not vary much between X-ray images.

It is considered what takes place by the profile trimming processing as to the solitary island A relative to the metal piece m4. The profile trimming processing is the image processing so as to trim the profile of the metal piece m4. Accordingly, the profile trimming at the position near the center of the intermediate region C, indicated as the point p in FIG. 13(A), will be executed from two directions. Specifically, one trimming is in the direction toward the low side from the point p so as to trim the main body of the metal piece m4 Another trimming is in the direction toward the upper side from the point p so as to trim the solitary island A. The solitary island A would disappear by the upper side trimming.

The inventor sets forth the rationale therefor. The width of the solitary island A in the crossing-over direction relative to the intermediate region C is less than a half width of the intermediate region C. Because the protrusion A appeared in the binarization image P2*a* is the pixel assigned as the less exposed pixel by the binarization processing and the size thereof per se is within the width of the intermediate region C. Accordingly, it will be understood that the profile trimming processing might just trim the metal piece m4 with the thickness as the same as just half width of the intermediate region C from near the center of the intermediate region C. If the strength of the profile trimming processing is quad hoc, the solitary island A less than the half thickness of the intermediate region C can be assuredly trimmed.

Figure 14A:
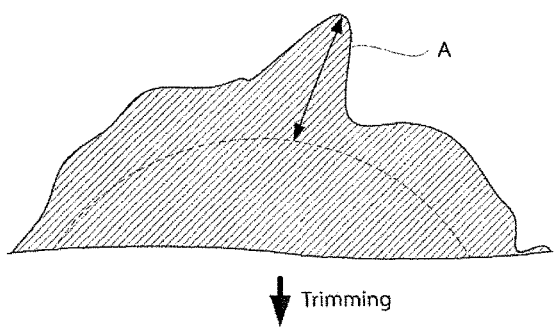
FIGS. 14(A) and 14(B) are schematic diagrams illustrating a profile trimming processing of Embodiment 1.
Figure 14B:
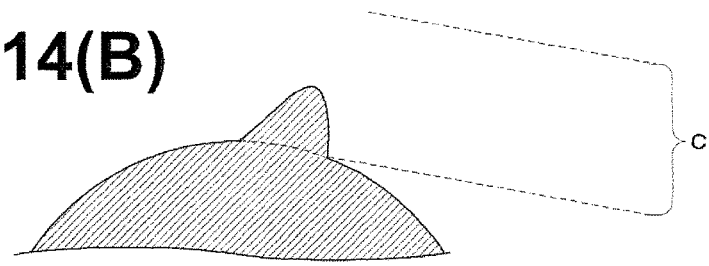

The profile trimming processing is executed relative to the synthetic image P4*a* in this way and the periphery of the metal piece can be assuredly trimmed. FIG. 14(A)(B) are illustrating the case in which the profile trimming processing is directly executed to the binarization image P2*a*. This time, the binarization image P2*a* includes the protrusion A. The protrusion A is not like a solitary island as the case of the synthetic image P4*a* and rather is like a peninsula protruded from the metal piece main body. When the profile trimming processing is executed on such binarization image P2*a*, a region of the stick-out region is remained without being scraped off as illustrated in FIG. 14(B). The profile trimming processing is an image processing so as to scrape off the layer having the fixed thickness relative to an image on the image. Accordingly, if the protrusion A is like a peninsula, the stick-out region of this region is too thick, as indicated by the arrow, to be completely trimmed by the profile trimming processing. This mode is not desirable from the accuracy standpoint of the image processing Then, it is supposed that the profile trimming processing so as to trim rather thick may be appropriate to trim completely the protrusion A. However, if such processing is executed, regions other than the protrusion A relative to the metal piece may be trimmed too much and the number of pixels to be processed with the graph cut processing element 16 in the later clause increases. This mode is not desirable from the speeding-up standpoint of the image processing.

In contrast, according to the present invention, if the profile trimming processing is executed on the synthetic image P4*a*, the stick-put region can be trimmed from the center of the intermediate region C exposed by the superimposing the edge E. That is, the thickness of the stick-out region relative to a periphery of the metal piece is uniform so that the stick-out region having a uniform thickness can be scraped off to be able to trim the stick-out region exactly.

Consequently, the profile trimming metal map P5*a* can be generated, wherein the stick-out region remained in the synthetic image P4*a* is trimmed. The map represents distribution of the metal piece on the original image P0 and no other element than the metal piece exists in the region certified as the metal piece. However, the map is just a mapping as for the region certified assuredly as the metal piece on the original image P0. The profile trimming metal map P5*a* takes care as the pixels in-place in the intermediate region C does not comprise a metal piece.

Figure 15A:
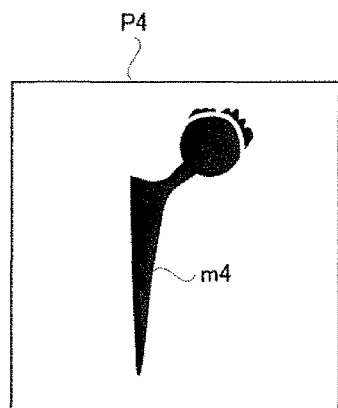
FIGS. 15(A) and 15(B) are schematic diagrams illustrating a profile trimming processing of Embodiment 1.
Figure 15B:
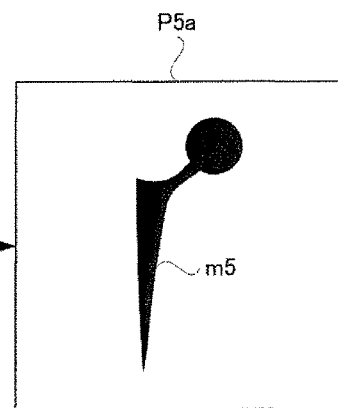
Figure 16A:
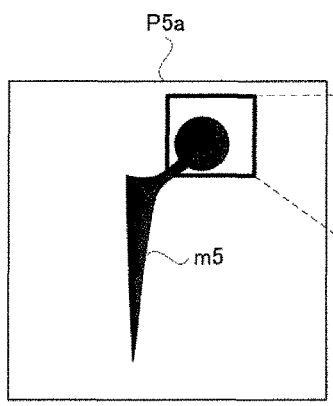
FIGS. 16(A) and 16(B) are schematic diagrams illustrating a profile trimming processing of Embodiment 1.
Figure 16B:
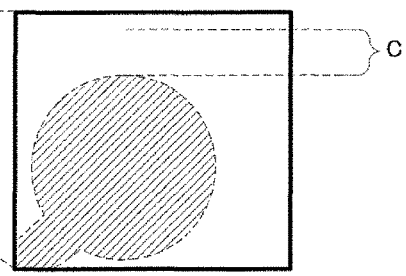

FIG. 15(A)(B) are illustrating the aspect, wherein the profile trimming metal map P5*a* is generated from the synthetic image P4*a* by the above profile trimming processing. Referring to FIG. 15(A)(B), the metal piece m5 on the map gets one size smaller than the metal piece m4 with the trimming operation. Further, when the synthetic image P4*a* is generated, the small solitary island born by dividing the metal piece m2 with the edge E is trimmed in the profile trimming metal map P5*a*. And FIG. 16(A)(B) are expanded views illustrating a region of profile trimming metal map P5*a*. Referring to FIG. 16(B), the metal piece m5 does not include the intermediate region C.

Operation of Image Synthesis Element 14 and Profile Trimming Element 15: Generation of the Profile Trimming Metal Map 5*a*

The image synthesis element 14 and the profile trimming element 15 execute the same operation as to the inversion binarization image P2*b*. The inversion binarization image P2*b* should incorporate other regions more exposed to X-ray than the metal piece. However, the binarization processing cannot provide an exact aspect of the region other than the metal piece m0. The rational is as is illustrated referring to FIG. 4(A)(B). That is, if the binarization processing is executed on the intermediate region C, an erroneous recognition of the decision as to whether belonging to the region other than the metal piece or not may take place.

Then, the image synthesis element 14 and the profile trimming element 15 execute the same operation on the inversion binarization image P2b as the operation on the binarization image P2a; and generate the profile trimming non-metal map P5b, wherein the pixels in-place in the intermediate region C relative to inversion binarization image P2b are trimmed from regions other than the metal piece. Specifically, the image synthesis element 14 generates a synthetic image P4b related to inversion, wherein the image on the inversion-binarization image P2b is divided near the center region of the intermediate region by superimposing the inversion-binarization image P2b and the edge extraction image P3. And the profile trimming element 15 generates a profile trimming non-metal map P5b, wherein the intermediate region C is trimmed from the instant image by trimming the profile of the image on the synthetic image P4b relative to inversion.

Figure 17A:
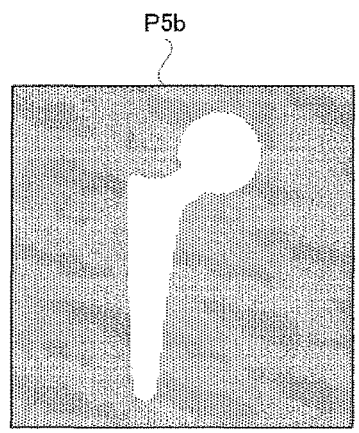
FIGS. 17(A) and 17(B) are schematic diagrams illustrating a map of Embodiment 1.

The map represents distribution of regions other than metal piece m0 on the original image P0 and no metal piece m0 exists in the mix in the region certified as the region other than the metal piece m0. However, the map is just a mapping as for the region certified assuredly as regions other than the metal piece on the original image P0. The profile trimming non-metal map P5a takes care as the pixels in-place in the intermediate region C does not comprise regions other than the metal piece. The generated profile trimming non-metal map P5b in this way is illustrated in FIG. 17(A).

Figure 17B:
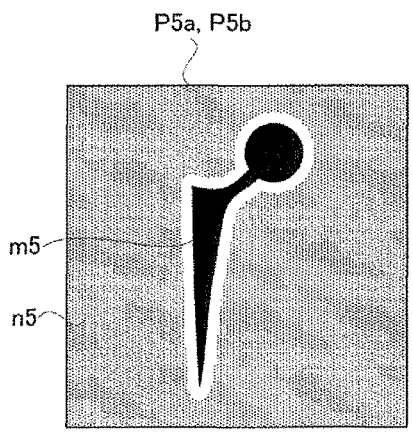

FIG. 17(B) is a view illustrating superimposing the profile trimming metal map P5a and the profile trimming non-metal map P5b. Referring to the superimposed view, it is noticed that the intermediate band between the metal piece m5 and the non-metal region n5 appears belonging to neither. Referring to the view, the white band is exactly the intermediate region C difficult to be decided as to whether the band belongs to the metal piece or not. The decision as to the pixels constituting the intermediate region C is made by the following image processing.

Operation of Graph Cut Processing Element 16

The filter processing image P1, the profile trimming metal map P5a and the profile trimming non-metal map P5b are sent to the graph cut processing element 16. The graph cut processing element 16 analyzes pixels belonging to the intermediate region C by the graph cut processing based on these images. The graph-cut-processed pixels are exactly assigned to either the metal piece or the non-metal region based on belongingness. The graph cut element 16 generates an extraction image P6, wherein the image of the metal piece m1 incorporated into the filter processing image P1 is extracted by executing a graph cut processing relative to the filter processed image P1 while recognizing that the filer processed image P1 on the profile trimming metal map P5a constitutes a part of the metal piece m1 incorporated into the filter processed image P1. The graph cut element 16 also executes a graph cut processing relative to the filter processing image P1 while recognizing as the image on the profile trimming non-metal map P5b constitutes a part of regions other than the metal piece m1 incorporated into the filter processing image P1.

FIG. 18(A)(B) are illustrating the mode of a node n used for the graph cut method. It is given that the image comprises the pixel two dimensionally arrayed as illustrated in FIG. 18(A). The graph cut method interprets as the pixel a is the node n connected each other. Each node corresponds to each pixel a. Accordingly, nodes n are two dimensionally arrayed. Each node n that is two dimensionally arrayed is connected to the adjacent node n each other. The connected node n each other is closely related each other and make up a lump. Then, the lump uniformly made of the entirety of image is dissolved into two lumps by gradually disconnecting each node n respectively. Consequently, one of dissolved two lumps only comprises the node n corresponding to the pixel belonging to the metal piece. The other lump comprises only the node n corresponding to the pixel belonging to non-metal region.

FIG. 19(A)(B) are illustrating the first step of the graph cut method. For ease of explanation, the inventor sets forth while extracting the line of the node n having the reference R1 in FIG. 18(B). Firstly, two nodes na, nb are added in addition to the node n corresponding to the pixel a. The node na is a virtual node representing the pixel belonging to the metal piece. The node na is connected to all nodes n. The node nb is a virtual node representing the pixel belonging to the non-metal region. The node nb also is connected to all nodes n.

Next, the graph cut processing element 16 assigns the node n referring to the profile trimming metal map P5a and the profile trimming non-metal map P5b. Consequently, the node n corresponding to the pixel deemed belonging to the metal piece relative to the profile trimming metal map P5a can be strongly connected to the node na and disconnected from the node nb. Also, the node n corresponding to the pixel deemed belonging to the non-metal region relative to the profile trimming non-metal map P5b can be strongly connected to the node nb and disconnected from the node na. Such operation is not considered as a load for the calculation device bringing graph cut method in reality.

Figures 20A, 20B:
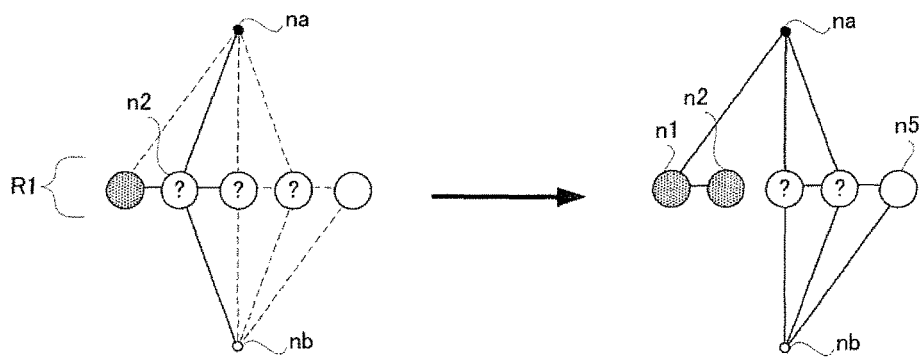
FIGS. 20(A) and 20(B) are schematic diagrams illustrating a graph cut processing of Embodiment 1.

Next, finally, an assignment operation relative to the pixels belonging to the intermediate region C will commence. Referring to FIG. 20(A)(B), the node n2 so-to-speak belonging to intermediate region C is not certified at all relative to neither the map P5b nor P5a. The graph cut processing element 16 notices the connection lines connected to the node n2. An evaluation value called cost is assigned to these lines. The graph cut processing element 16 divides the connection lines by comparing the costs. The cost is decided based on the pixel value of the pixel corresponding to the node n. Specifically, in the case of adjacent pixels having a similar pixel value, the cost of the connection line between nodes n corresponding to adjacent pixels is set as low. Then, in the case of the pixel value of a pixel, which is a value representing less X-ray exposure, the cost of the connection line between node n and the node na corresponding to the instant pixel will be set as low. Also, in the case of the pixel value of a pixel, which is a value representing large X-ray exposure, the cost of the connection line between node n and the node nb corresponding to the instant pixel will be set as low. Accordingly, the low cost represents the close relationship between respective nodes.

The graph cut processing element 16 repeatedly divides the connection line while keeping the low cost connection lines. For example, referring to the embodiment of FIG. 20(A)(B), the node n2 is disconnected from the node n on the right and the node nb and then the corresponding pixel a is judged as belonging to the metal piece. Such processing relative to the connection line should be a big load to the calculation device to bring graph cut method into reality.

FIG. 21(A)(B) are illustrating that the divided node n by the graph cut method is turned back as an image. In this way, the generated figure is called as the extract image P6, wherein the metal piece incorporated into the original image P0 is extracted. The expanded extraction image P6 preciously represents the metal piece aspect having a smooth aspect. The extraction image P6 is the image, wherein the metal piece relative to the intermediate region C is also accurately extracted.

Operation of Color Tone Correction Element 17

The extraction image P6 is sent to the color tone correction element 17. The color tone correction element 17 generates the color tone correction image P7 by correcting the color tone on the original image P0 referring to the extraction image P6. At this time, the color tone correction element 17 executes the dynamic range processing and the contrast adjustment processing on the region excluding the metal piece on the original image P0. FIG. 22(A)(B) are illustrating the mode thereof. As illustrated in FIG. 22(A)(B), the color tone correction element 17 is only operative for regions other than the metal piece, depicted as the oblique lines on the original image P0. At this time, the metal piece incorporated into the original image P0 does not comprise the original image. Accordingly, the color tone correction element 17 will not only read a pixel value but also not convert the pixel value.

The color tone correction element 17 converts the pixel value of pixels in-place in the oblique line region in FIG. 22(A) to the one having high visual recognition. The pixel value of pixels in-place in the oblique region relative to the original image P0 is similar and the difference between respective pixels is vague. The pixels belonging to the oblique region under such circumstance are in that the difference of the pixel value is enhanced by the color tone correction. Accordingly, the color tone correction image P7 generated by color tone correction would have high visual recognition. Certainly, the color tone correction image P7 is out of the processing on the metal piece. This fact is desirable to increase the visual recognition of the color tone correction image P7. Because the metal piece is not concerned by a person in charge of diagnosis and the visual recognition of regions other than the metal piece would never decrease by the impact of the extreme pixel value originated in the metal piece upon the color tone correction. Accordingly, the color tone correction element 17 executes the color tone correction processing on regions other than the metal piece relative to the original image P0 referring to the extraction image P6.

According to the image processing device of the present invention, a color tone correction having both assuredness and high-speed can be executed. Specifically, the image processing device of the present invention decides by executing a graph cut processing whether the intermediate region between the region exposed more to radiation and the region exposed less thereto relative to the original image P0 is belonging to the metal piece or not. Accordingly, the profile of the metal piece incorporated into the original image P0 can be exactly extracted. The graph cut processing is highly reliable but has a drawback as calculation load therefor might be high. Then, according to the present invention, the calculation load is extremely lowered with some devices.

Specifically, the image processing device of the present invention comprises: a binarization element 12a that generates a binarization image incorporating a rough metal piece incorporated into the original image by binarization of the original image; an edge extraction processing element 13 that extracts the position near the center of the intermediate region C on the original image P0; an image synthesis element 14 that generates a synthetic image P4a, wherein an image on the binarization image P2a is divided near the center region of the intermediate region C; and a profile trimming element 15 that trims the intermediate region by trimming the profile of the image on the synthetic image P4a. According to each means, the inside aspect of the metal piece incorporated into the original image P0 can be exactly extracted. The inside aspect comprises certainly the metal piece without executing a graph cut processing so that the graph cut processing of such region can be skipped.

It is desirable that the profile trimming processing is suppressed as minor as possible from the high-speed image processing standpoint. According to the present invention, the system executes an image trimming from near the center of the intermediate region so as to minimize the profile trimming processing after the image on the binarization image P2a is divided near the center of the intermediate region. Followingly, the range subjected to the image trimming can be as small as possible. Consequently, the number of pixels on which the graph cut processing relative to the original image P0 executes decreases and the image processing can be highly speeded up.

Further, If the original image P0 to which the binarization processing element 12a, the edge extraction means and the graph cut processing element 16 are referring is executed by the median filter, the noise component appeared in the original image P0 is trimmed by the median filer so that the metal piece incorporated in the original image P0 can be more exactly extracted.

Further, the edge extraction element can extract assuredly near the center of the intermediate region by executing Laplacian filter on the original image P0. Because Laplacian filter is spacial differential filter.

The above system illustrates the operation of the other region than the metal piece on the original image. Specifically, the image processing device of the present invention comprises; a step of generating an inversion binarization image P2b incorporating a rough image of other region than metal piece incorporated into the original image by binarization of the original image; a step of generating a synthetic image P4b relative to the inversion, wherein the image on the inversion binarization image P2b is divided near the center region of the intermediate region C based on the above step, and then after a step of trimming the intermediate region from the image on the synthetic image P4b relative to the inversion by trimming the profile of the image on the synthetic image P4b relative to the inversion.

Accordingly, the inside aspect of other regions than the metal piece incorporated into the original image P0 can be assuredly extracted by each means. The inside aspect comprises certainly regions other than the metal piece without executing a graph cut processing so that the graph cut processing of such region can be skipped.

It is desirable that the profile trimming processing is suppressed as minor as possible from the high-speed image processing standpoint. According to the present invention, the system executes an image trimming from near the center of the intermediate region so as to minimize the profile trimming processing after the image on the binarization image P2a is divided near the center of the intermediate region. Followingly, the range subjected to the image trimming can be as small as possible. Consequently, the number of pixels on which the graph cut processing relative to the original image P0 executes decreases and the image processing can be highly speeded up.

Embodiment 2

Next, the inventor sets forth an image processing of Embodiment 2. The system of Embodiment 2 is the device that can make the tomographic image clear with the image processing device of the present invention. Here, the tomographic image that is incorporating an image obtained when the subject is sliced at a cross section is generated by using a radiographic device. The image processing device 22 of Embodiment 2 comprises each element 11, 12a, 12b, 13, 14, 15, 16 of Embodiment 1. It will be noticed that the image processing device 22 of Embodiment 2 does not comprise the color tone correction element 17, differently from Embodiment 1.

The inventor sets forth the radiation tomographic device of Embodiment 2 operable to generate a tomographic image referring to FIGS. Further, X-ray of Embodiment is the radiation of the present invention. Further, FPD stands for Flat Panel X-ray Detector. The X-ray imaging device 50 of the present invention is for observation of artificial joint replacement surgery during the prognosis thereafter.

Figure 23:
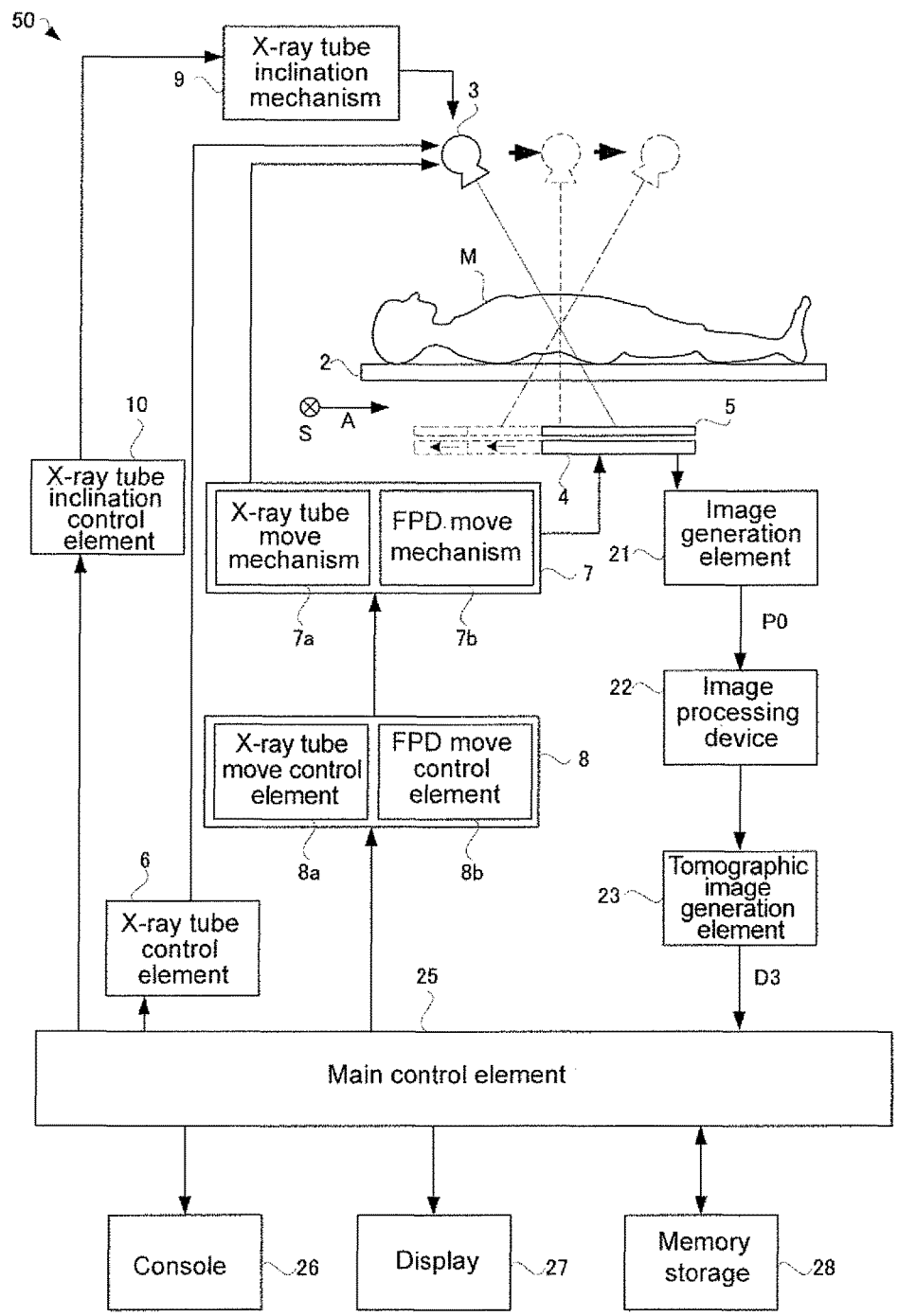
FIG. 23 is a functional block diagram illustrating the system of the X-ray tomographic device of Embodiment 2.

FIG. 23 is a functional block diagram illustrating the system of the X-ray imaging device 50 of Embodiment 2. Referring to FIG. 23, an X-ray imaging device 50 of Embodiment 2 comprises; a table 2 on which the subject M subjected to X-ray tomography is loaded, an X-ray tube 3 that is installed upper side of the table 2 (the first surface of the table 2) and radiates corn-like X-ray beam toward the subject M, a FPD 4 that is installed lower side of the table 2 (ground side of the table 2) and detects X-ray transmitting through the subject M, a synchronization move mechanism 7 that allows the X-ray tube 3 and the FPD 4 to make a synchronization move in the opposite direction each other while sandwiching the target region of the subject M under the condition in which the center axis of the cone-like X-ray beam always coincides with the center of the FPD 4, a synchronization move control element 8 that controls the synchronization move mechanism 7, and an X-ray grid that absorbs the scattered X-ray set as covering the X-ray detection surface of the FPD 4 to detect X-ray. In this mode, the table 2 is in-place in the position sandwiched by the X-ray tube 3 and the FPD 4.

The synchronization move mechanism 7 comprises the X-ray tube move mechanism 7a that moves the X-ray tube in the body axis direction A relative to the subject M and the FPD move mechanism 7b that moves the FPD 4 in the body axis direction A relative to the subject M. Further, the synchronization move control element 8 comprises the X-ray tube move control element 8a that controls the X-ray tube move mechanism 7a and the FPD move control element that controls the FPD move mechanism 7b. When the original image P0 is continuously imaged, the synchronization move control element 8 moves the X-ray tube and the FPD 4 in the opposite direction each other.

The X-ray tube radiates structure-wise cone-like pulse X-ray beam to the subject M repeatedly in accordance with control by the X-ray tube control element 6. The collimator is attached to the X-ray tube to collimate the X-ray beam to cone shape like a pyramid. And the X-ray tube 3 and the FPD 4 form the imaging system that images the X-ray projection image. The X-ray control element 6 controls the X-ray tube according to the predetermined values specifying tube electric current, tube electric voltage and pulse width thereof.

The synchronization move mechanism 7 comprises a step of moving the X-ray tube and the FPD 4 in synchronization relative to the subject M. The synchronization move mechanism 7 moves straight the X-ray tube 3 along the straight line trajectory (longitudinal direction of the table 2) parallel to the body axis direction A of the subject M in accordance with control by the synchronization move control element 8. The move directions of the X-ray tube and the FPD 4 coincide with the longitudinal direction of the table 2. In addition, during the examination, the cone-like X-ray beam radiated from the X-ray tube 3 is always radiated toward the target region of the subject M and the X-ray radiation angle thereof e.g. can be changed from the initial angle −20° till the final angle 200 by changing angle of the X-ray tube 3. Such change of X-ray radiation angle can be performed by the X-ray tube inclination mechanism 9. The X-ray tube inclination control element 10 is installed so as to control the X-ray tube inclination mechanism 9.

And the X-ray imaging device 50 of Embodiment 2 further comprises a main control element 25 that controls comprehensively each control element 6, 8, 10, 11, 12 and a display 27 that displays a tomographic image. The main control element 25 comprises a CPU and brings each control element 6, 8, 10 and each element 21, 22, 23, set forth later, into reality by executing a variety of programs. The memory element 28 stores all data related to control of the X-ray imaging device, e.g. parameters related to the control of the X-ray tube 3. The console 26 is used to input each operation relative to the X-ray imaging device 50 by the operator.

Further, the synchronization move mechanism 7 moves straight the FPD 4 installed under side of the table 2 in the straight line of the body axis direction A (longitudinal direction of the table 2) in synchronization of straight move of the X-ray tube 3 as set forth above. And the move direction is opposite direction to the move direction of the X-ray tube 3. Specifically, the cone-like X-ray beam in changing the position of the focal point of the X-ray tube 3 and the radiation direction along with move of the X-ray tube 3 are structure-wise always received with all surface of the detection surface of the FPD4. Accordingly, the FPD 4 can receive e.g. 74 projection images while moving in the opposite direction relative to the X-ray tube 3 each other in synchronization during one examination. Specifically, referring to FIG. 23, the imaging systems 3, 4 move from the initial position illustrated as a solid line to the position illustrated as a dashed-line via the position illustrated as a broken line facing each other. Specifically, a plurality of X-ray projection images are taken while changing the positions of X-ray tube 3 and the FPD 4. By the way, the cone-like X-ray beam always are received by all surfaces of the detection surface of the FPD 4 so that the center axis of the cone-like X-ray beam during imaging always coincides with the center point of the FPD 4. Further, the center of the FPD 4 moves straight and such move is in the opposite direction relative to the move of the X-ray tube 3. That is, it will be understood that the system moves the X-ray tube 3 and the FPD 4 in synchronization and in the opposite direction each other along the body axis direction A.

Principal of Acquisition of Tomographic Image

Figure 24:
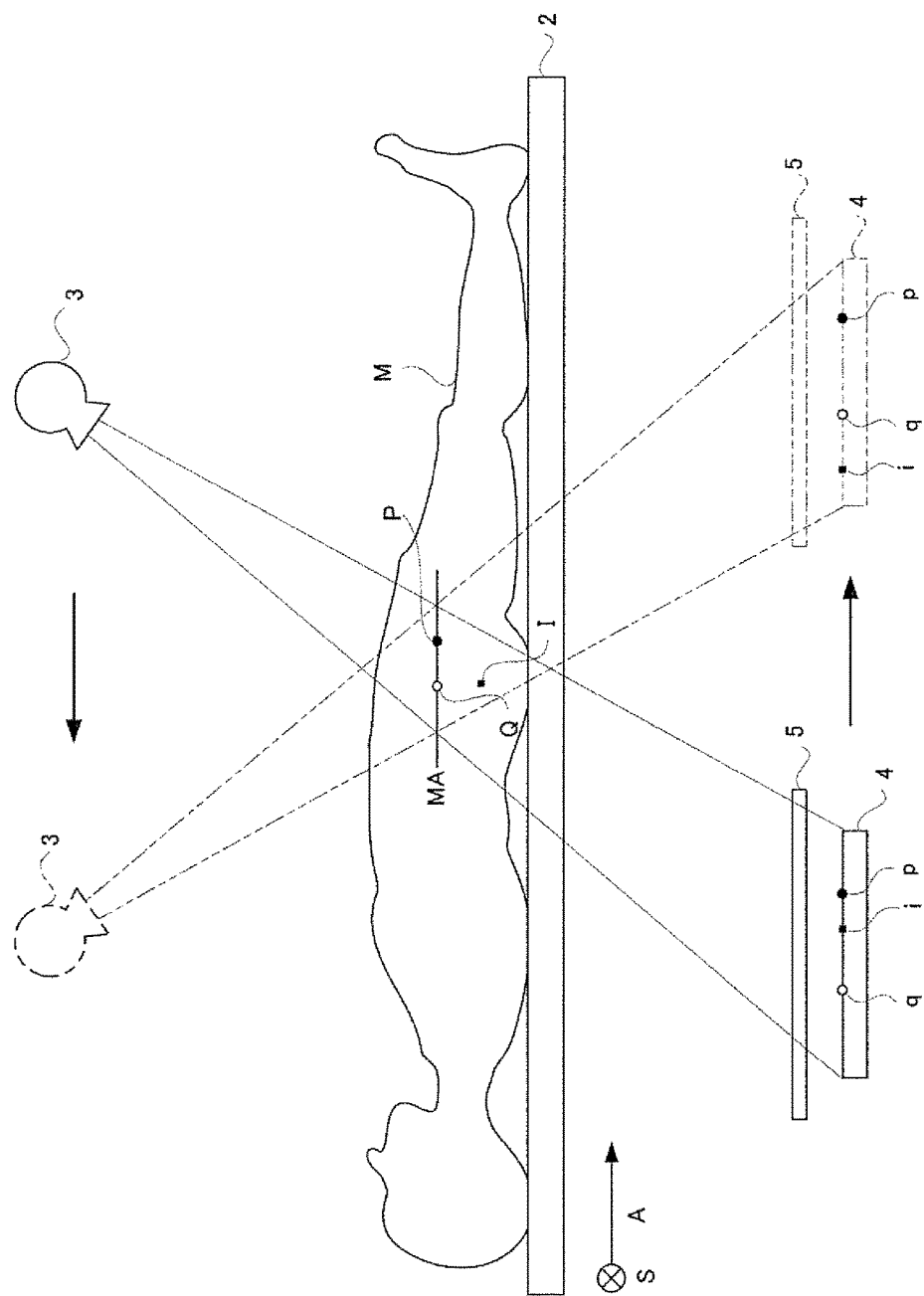
FIG. 24 is a schematic diagram illustrating an acquisition principle of the tomographic image of Embodiment 2.

Next, the inventor sets forth the principal of acquisition of tomographic image of Embodiment 2. According to the system of Embodiment 2, the tomographic image can be generated by generating a plurality of the tomographic images that are images taken when the subject M is sliced on the plan. FIG. 24 is a schematic diagram illustrating the acquisition method for the tomographic images taken by the X-ray imaging device of Embodiment 2. For example, referring to FIG. 24, as the virtual plan (the base slice section MA) parallel to the table 2 (horizontal relative to the perpendicular) is set forth, a series of the original image P1, P2 is generated by the image generation element 21 while the FPD 4 moves in synchronization in the opposite direction relative to the X-ray tube according to the radiation direction of the cone-like X-ray beam from the X-ray tube 3 so that the points P, Q in-place on the base slice section can be always projected to the fixed-points p, q on the X-ray detection surface of the FPD 4. The projection images of the subject M are incorporated into the series of the original image P1, P2 while changing the position thereof. Then, providing the series of original image P1, P2 are reconstructed by the tomographic image generation element 23, the images (e.g. fixed point p, q) in-place on the base slice section MA are accumulated and the X-ray tomographic image can be imaged. On the other hand, the point I in-place out of the base slice section MA is incorporated into the series of images of the subject M as a point i while changing the projection position on the FPD 4. The point i, differently from the fixed points p, q, will not focus into an image and will be out of focus at the step of superimposing the X-ray projection images by the tomographic image generation element 23. Accordingly, the series of projection images are superimposed so that the X-ray tomographic image incorporating only the image in-place on the base slice section MA of the subject M can be obtained. Accordingly, the projection images are simply superimposed so that the tomographic image on the base slice section MA can be obtained. The tomographic image generation element 23 corresponds to the tomographic image generation means of the present invention.

Further, the tomographic image generation element 23 can obtain the same tomographic image at any slice section horizontal to the base slice section MA. During imaging, the projection position of the point i relative to the FPD 4 moves but the move rate increases according to increasing distance between the point I before projection and the base slice surface MA. If the obtained series of images of the subject M should be reconstructed while shifting to the body axis direction A at the predetermined pitch utilizing this fact, the tomographic image at the slice section parallel to the base slice section MA can be obtained. Such reconstruction of a series of tomographic image can be executed by the tomographic image generation element 23.

Operation of X-ray Imaging Device 50

Next, the inventor sets forth the operation of X-ray imaging device. The first operation of the X-ray imaging device is operative to load the subject M. Then, when the operator provides the instruction to commence the imaging for the original image P0 through the console 26, X-ray radiation from the X-ray tube 3 would start. At this time, referring to FIG. 23, the imaging systems 3, 4 move from the position illustrated as a solid line to the position illustrated as a dashed-line via the position illustrated as the broken line. While this time, 74 original images P0 are obtained and sent to the image processing device 22. The image processing device 22 comprehensively represents each component 11, 12*a*, 12*b*, 13, 14, 15, 16 as set forth in Embodiment 1. The image processing device 22 generates 74 extraction images P6 by the binarization processing of each of 74 original images P0 (referring to FIG. 25(A)(B)). The extraction image P6 is the binarization image from which the metal piece incorporated into the original image P0 is extracted.

According to the description as to the principal of the tomographic image generation referring to FIG. 24, the tomographic image can be obtained if the tomographic image generation element 23 executes the image reconstruction processing for the 74 original images P0. Accordingly, if only generation of tomographic image is expected, no generation of the extraction image P6 by the image processing device 22 is needed. However, if the original image P0 should be simply reconstructed, the tomographic image having an false image can be only obtained. Because each original image P0 is incorporating the metal piece. The metal piece thereof cannot be fully obfuscated by superimposition of the original image P0 because of the extreme pixel value. Accordingly, a residual image of the metal piece that cannot be completely canceled by superimposition of images may appear in the periphery of the metal piece of the tomographic image. The residual image thereof is the real identity of the false image appeared in the tomographic image.

Figure 27A:
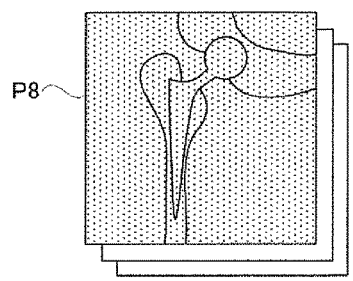
FIGS. 27(A) and 27(B) are schematic diagrams illustrating an acquisition operation of the tomographic image of Embodiment 2.
Figure 27B:
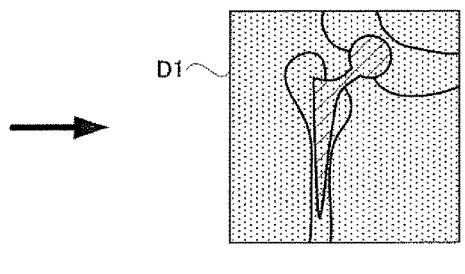

The X-ray tomographic device of Embodiment 2 is a device in which such false image of the tomographic image would not take place. Specifically, the X-ray tomographic device of Embodiment 2 is the device in which no false image appears in the tomographic image by superimposing the metal piece based on the function of the image processing device 22. Specifically, the tomographic image according to Embodiment 2 cannot be generated by superimposing as-is the original image P0. Specifically, referring to FIG. 25(A)(B), the tomographic image is generated by the tomographic image generation element 23 referring to the extraction image P6 in which the metal piece is extracted from each of the original image P0. The extraction image P6 is the image in which the image processing device 22 executes the extraction processing of the metal piece relative to each of 74 original images P0. Accordingly, 74 extraction images P6 will be generated Operation of the Tomographic Image Generation Element 23: Metal Piece Cancel Processing The tomographic image generation element 23 generates the tomographic image referring to the extraction image P6 generated by the image processing device 22. The mode thereof is specifically set forth. First, the tomographic image generation element 23 executes the image processing so as to cancel the image of the metal piece incorporated into each of the original image P0. Specifically, referring to FIG. 26(A)(B)(C), the tomographic image generation element 23 understands the position/size/range of the metal piece incorporated into the original image P0 by referring to the extraction image P6. And the tomographic image generation element 23 converts the pixel value of pixels inside metal piece to the pixel value of pixels in the periphery of the metal piece. Then, the pixel value related to the conversion is e.g. an average value of pixels in the periphery of the metal piece. Accordingly, the metal piece cancel image P8 can be generated as if the metal piece incorporated into the original image P0 is assimilated in the periphery. The metal piece cancel image P8 is generated corresponding to each of 74 original images P0. Accordingly, the image processing device 23 performs the metal piece cancel processing, wherein a metal piece cancel image P8 is generated by cancel the metal piece incorporated into the original image P0 from the original image P0, referring to the extraction image P6 in which the metal piece is extracted from each original image continuously imaged while changing the imaging direction relative to the subject M, Operation of the Tomographic Image Generation Element 23: Generation of Metal Piece Cancel Tomographic Image Referring to FIG. 27(A)(B), the tomographic image generation element 23 generates the tomographic image by executing the image reconstruction processing on 74 metal piece cancel images P8. The image generated at this time is called as the metal piece cancel tomographic image D1 for discrimination purpose. The metal piece cancel tomographic image D1 is generated by executing the image reconstruction processing on the image as if the metal piece assimilated with the periphery of the metal piece so that no false image will appear in the periphery of the metal piece. However, the region corresponding to the metal piece illustrated in the inclination region of the metal piece cancel tomographic image D1 in FIG. 27(B) is completely filled up with incorrect pixel value. Because the pixel value of the pixel inside the metal piece relative to the metal piece cancel image P8 that is a base of the metal piece cancel tomographic image D1 is converted to the pixel value different from the right pixel value. Hereafter, the tomographic image generation element 23 is operative to bring the pixel value of the metal piece region relative to the metal piece cancel tomographic image D1 closer to the right pixel value. The tomographic image generation element 23 performs the metal piece cancel tomographic image generation processing that generates the metal piece cancel tomographic image D1 by executing an image reconstruction processing on a plurality of the metal piece cancel image P8, Operation of the Tomographic Image Generation Element 23: Metal Piece Trimming Processing Specifically, the tomographic image generation element 23 performs a different image processing on the 74 original images P0. Referring to FIG. 28(A)(B)(C), the tomographic image generation element 23 subtracts the corresponding metal piece trimming image P8 from each of the original image P0. The original image P0 and the metal piece cancel image P8 have the same image as the region other than the metal piece so that the same regions are canceled and erased by the subtraction processing. Specifically, the trimming image P9 is generated as if the region corresponding to the metal piece is trimmed from each of original image P0 by the subtraction processing of the tomographic image generation element 23. The trimming image P9 is more different than the above extraction image P6 that might be first surmised similar. The extraction image P6 is a binarization image and represents the aspect of the metal piece on the original image P0 but, on the other hand, the trimming image P9 represents not only the aspect of the metal piece but also light and shade inside the metal piece. Specifically, the metal piece of the trimming image P9 looks like a thinner metal piece incorporated into the original image P0. Because when respective images are subject to subtraction processing, the pixel value (pixel value of pixels in the periphery of the metal piece relative to the original image P0) of the metal piece of the metal piece trimming image P8 is subtracted from the pixel value of pixels on the metal piece of the original image P0. Accordingly, the tomographic image generation element 23 performs the metal piece trimming processing that generates a trimming image P9 by taking out the corresponding regions to the metal piece from each of the original image referring to the extraction image P6.

Figure 29A:
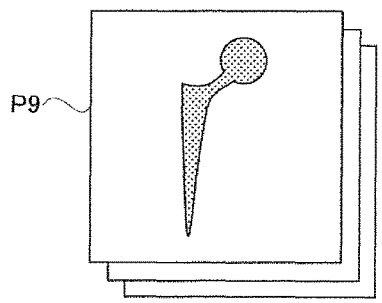
FIGS. 29(A) and 29(B) are schematic diagram illustrating an acquisition operation of the tomographic image of Embodiment 2.
Figure 29B:
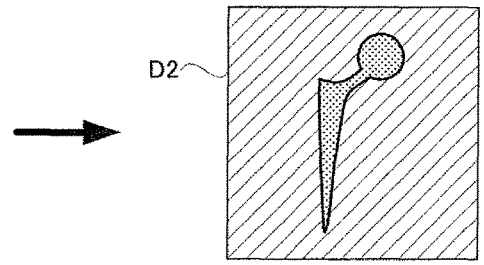

Operation of the Tomographic Image Generation Element 23: Generation of Metal Piece Tomographic Image Referring to FIG. 29(A)(B), the tomographic image generation element 23 generates the tomographic image by executing the image reconstruction processing on 74 tomographic images P9. The image generated at this time is called as the metal piece tomographic image D2 for image discrimination purpose. The metal piece tomographic image D2 is the tomographic image that shares the slice section with the metal piece cancel tomographic image D1. Further, the metal piece tomographic image D2 is generated by executing the image reconstruction processing on the image into which the only metal piece is incorporated so that the tomographic image of the metal piece can be incorporated. Accordingly, referring to FIG. 29(B), the region corresponding to the periphery of the metal piece, illustrated as the inclination region of the metal piece tomographic image D2, is not imaged at all. Accordingly, the tomographic image generation element 23 executes the metal piece trimming tomographic image generation processing that generates the metal piece tomographic image D2 by executing an image reconstruction processing on a plurality of the trimming image P9

Operation of the Tomographic Image Generation Element 23: Addition of Tomographic Image Accordingly, the tomographic image generation element 23 generates the tomographic images in two different modes. Referring to last FIG. 30(A)(B)(C), the tomographic image generation element 23 performs the addition of the tomographic images D1, D2 thereof. The image generated at this time is called as the synthetic tomographic image D3 for image discrimination purpose. The synthetic tomographic image D3 provides a superior visual recognition. Specifically, regions other than the metal piece of the synthetic tomographic image D3 is originated in the metal piece cancel tomographic image D1 so that no false image can appear. Then, the metal piece region of the synthetic tomographic image D3 is originated in the metal piece tomographic image D2 so that the reliability of the pixel value can be high. Accordingly, the tomographic image generation element 23 generates the synthetic tomographic image D3 by adding the metal piece cancel tomographic image D1 and the metal piece tomographic image D2. The synthetic tomographic image D3 is displayed on the display 27 and then the operation of Embodiment 2 can be completed.

Accordingly, the image processing device 1 of the present invention can be used for generation of the tomographic image.

The present invention is not limited to the above system and further following alternative Embodiment can be implemented.

(1) The above extraction element 13 is not limited to Laplacian filter and also operable using the differential filter for the edge extraction.

(2) The above profile trimming element 15 obtains the trimming intensity that is obtained by actual measurement of the width of intermediate region C, but, instead of this constitution, may executes the profile trimming processing until trimming all solitary island appearing in the synthetic image P4a.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

INDUSTRIAL APPLICABILITY

As set forth above, the above invention is suitable for medicinal fields.

EXPLANATION OF REFERENCES

P0 Original image
P2a Binarization image
P2b Inversion binarization image
P3 Edge extraction image P4*a* Synthetic image
P4*b* Synthetic image relative to inversion
P5*a* Profile trimming metal map
P5*b* Profile trimming non-metal map
P6 Extraction image
11 Median filter processing element (Median filer processing means)
12*a* Binarization element (Binarization means)
12*b* Inversion element (Inversion means)
13 Edge extraction element (Edge extraction processing means)
14 Image synthesis element (Image synthesis means)
15 Profile trimming element (Profile trimming processing means)
16 Graph cut processing element (Graph cut processing means)
17 Color tone correction element (Color tone correction processing means)
23 Tomographic image generation element (Tomographic image generation means)

What is claimed is:

1. An image processing device, that operably executes an image processing on an original image incorporating a metal piece obtained by a radiation imaging of a subject having an implanted metal piece inside, comprises:
a binarization processor that operably generates a binarization image incorporating a rough metal piece incorporated into said original image by conducting a binarization of said original image;
an edge extraction processor that operably generates an edge extraction image, wherein a boundary indicating a position near a center of an intermediate region between a region exposed more to radiation and a region exposed less thereto relative to said original image is extracted by conducting an operable edge extraction processing on said original image;
an image synthesis processor that generates a synthetic image, wherein an image on said binarization image is operably divided near the center region of said intermediate region by superimposing said binarization image and said edge extraction image;
a profile trimming processor that generates a profile trimming metal map, wherein said intermediate region is trimmed from the image on said synthetic image by a trimming of the profile of the image on said synthetic image; and
a graph cut processor that generates an extraction image, wherein the image of the metal piece incorporated into said original image is extracted by executing a graph cut processing relative to said original image while recognizing that the image on said profile trimming metal map that constitutes a region of the metal piece incorporated into said original image.

2. The image processing device, according to claim 1, further comprising:
a median filter processor that operably executes a median filter relative to said original image,
wherein said original image is referred by said binarization processor, said edge extraction processor and said graph cut process or, and the median filter is executed on said original image.

3. The image processing device, according to claim 1, wherein:
said edge extraction process or is operative to execute a Laplacian filter to said original image.

4. The image processing device, according to claim 1 further comprising:
an inversion processor that generates an inversion-binarization image incorporating a plurality of rough image of regions other than the metal piece incorporated into said original image by operably executing the inversion processing relative to said binarization image, said image synthesis processor that generates a synthetic image,
wherein an image on said inversion-binarization image is divided near the center region of said intermediate region by superimposing said binarization image and said edge extraction image,
said profile trimming processor that generates a profile trimming non-metal map, wherein said intermediate region is trimmed from the image on said synthetic image by trimming the profile of the image on said synthetic image, and
said graph cut processor operably executes a graph cut processing relative to said original image while recognizing as the image on said profile trimming non-metal map constitutes a region of regions other than the metal piece incorporated into said original image.

5. The image processing device, according to claim 1, comprising:
a color tone correction processor operable to execute the color tone correction processing for the region other than the metal piece relative to said original image referring to said extraction image.

6. The image processing device, according to claim 1, comprising:
a metal piece cancel processor that generates a metal piece cancel image by operably canceling the metal piece incorporated into said original image from said original image referring to the extraction image, further comprising;
wherein the metal piece is operably extracted from each original image continuously imaged while changing the imaging direction relative to the subject;
a metal piece cancel tomographic image generation processor that operably generates a metal piece cancel tomographic image by executing an image reconstruction processing on a plurality of said metal piece cancel image; and
a metal piece trimming processor that operably generates a trimming image by taking out the corresponding regions to the metal piece from each said original image referring to said extraction image;
a metal piece tomographic image generation processor that operably generates metal piece tomographic image by executing an image reconstruction processing on a plurality of said trimming images; and
a tomographic image generation processor that operably executes the tomographic image adding processing so as to generate the synthetic tomographic image by adding said metal piece cancel tomographic image and the metal piece tomographic image.

7. An image processing device, that operably executes an image processing on an original image incorporating a metal piece obtained by a radiation imaging of a subject having an implanted metal piece inside, comprises:
a binarization processor that operably generates a binarization image incorporating a rough metal piece incorporated into said original image by conducting a binarization of said original image;
an edge extraction processor that operably generates an edge extraction image, wherein a boundary indicating a position near a center of an intermediate region between a region exposed more to radiation and a region exposed less thereto relative to said original image is extracted by conducting an operable edge extraction processing on said original image;
an image synthesis processor that generates a synthetic image, wherein an image on said binarization image is operably divided near the center region of said intermediate region by superimposing said binarization image and said edge extraction image;
a profile trimming processor that generates a profile trimming metal map, wherein said intermediate region is trimmed from the image on said synthetic image by a trimming of the profile of the image on said synthetic image;
a graph cut processor that generates an extraction image, wherein the image of the metal piece incorporated into said original image is extracted by executing a graph cut processing relative to said original image while recognizing that the image on said profile trimming metal map that constitutes a region of the metal piece incorporated into said original image;
a median filter processor that operably executes a median filter relative to said original image;
wherein said original image is referred by said binarization processor, said edge extraction processor and said graph cut processor, and the median filter is executed on said original image;
said edge extraction processor is operative to execute a Laplacian filter to said original image;
an inversion processor that generates an inversion-binarization image incorporating a plurality of rough image of regions other than the metal piece incorporated into said original image by operably executing the inversion processing relative to said binarization image, said image synthesis processor that generates a synthetic image;
wherein an image on said inversion-binarization image is divided near the center region of said intermediate region by superimposing said binarization image and said edge extraction image;
said profile trimming processor that generates a profile trimming non-metal map, wherein said intermediate region is trimmed from the image on said synthetic image by trimming the profile of the image on said synthetic image; and
said graph cut processor operably executes a graph cut processing relative to said original image while recognizing as the image on said profile trimming non-metal map constitutes a region of regions other than the metal piece incorporated into said original image.

8. The image processing device, according to claim 7, comprising:
a color tone correction processor module operable to execute the color tone correction processing for the region other than the metal piece relative to said original image referring to said extraction image.

9. The image processing device, according to claim 8, comprising:
a metal piece cancel processor that generates a metal piece cancel image by operably canceling the metal piece incorporated into said original image from said original image referring to the extraction image, further comprising;
wherein the metal piece is operably extracted from each original image continuously imaged while changing the imaging direction relative to the subject;
a metal piece cancel tomographic image generation processor that operably generates a metal piece cancel tomographic image by executing an image reconstruction processing on a plurality of said metal piece cancel image; and
a metal piece trimming processor that operably generates a trimming image by taking out the corresponding regions to the metal piece from each said original image referring to said extraction image;
a metal piece tomographic image generation processor that operably generates metal piece tomographic image by executing an image reconstruction processing on a plurality of said trimming images; and
a tomographic image generation processor that operably executes the tomographic image adding processing so as to generate the synthetic tomographic image by adding said metal piece cancel tomographic image and the metal piece tomographic image.

10. A method of operating an image processing device, that operably executes an image processing on an original image incorporating a metal piece obtained by a radiation imaging of a subject having an implanted metal piece inside, comprising the steps of:
generating with a binarization module a binarization image incorporating a rough metal piece incorporated into said original image by conducting a binarization of said original image;
generating with an edge extraction processing module an edge extraction image, wherein a boundary indicating a position near a center of an intermediate region between a region exposed more to radiation and a region exposed less thereto relative to said original image is extracted by conducting an operable edge extraction processing on said original image;
generating with an image synthesis module a synthetic image, wherein an image on said binarization image is operably divided near the center region of said intermediate region by superimposing said binarization image and said edge extraction image;
generating with a profile trimming module a profile trimming metal map, wherein said intermediate region is trimmed from the image on said synthetic image by a trimming of the profile of the image on said synthetic image;
generating with a graph cut module an extraction image, wherein the image of the metal piece incorporated into said original image is extracted by executing a graph cut processing relative to said original image while recognizing that the image on said profile trimming metal map that constitutes a region of the metal piece incorporated into said original image;
creating with a median filter processing module a median filter relative to said original image,
wherein during said steps of generating and creating, said original image is referred by said binarization processing module said edge extraction module and said graph cut processing module, and the median filter is executed on said original image; and
conducting with said edge extraction processing module a Laplacian filter to said original image.

11. The method of operating the image processing device, according to claim 10, further comprising the steps of:
generating with an inversion module an inversion-binarization image incorporating a plurality of rough image of regions other than the metal piece incorporated into said original image by operably executing the inversion processing relative to said binarization image,
generating with said image synthesis module a synthetic image, wherein an image on said inversion-binarization image is divided near the center region of said intermediate region by superimposing said binarization image and said edge extraction image, generating with a profile trimming module a profile trimming non-metal map, wherein said intermediate region is trimmed from the image on said synthetic image by trimming the profile of the image on said synthetic image, and generating with said graph cut module a graph cut processing relative to said original image while recognizing as the image on said profile trimming non-metal map constitutes a region of regions other than the metal piece incorporated into said original image.

12. The method of operating an image processing device, according to claim 11, further comprising the steps of:

generating with a color tone correction processing module a color tone correction processing for the region other than the metal piece relative to said original image referring to said extraction image.

13. The method of operating the image processing device, according to claim 12, further comprising the steps of:

conducting with a metal piece cancel processing module a metal piece cancel image step by operably canceling the metal piece incorporated into said original image from said original image referring to the extraction image, further comprising the steps of;

extracting the metal piece is operably from each original image continuously imaged while changing the imaging direction relative to the subject;

operating a metal piece cancel tomographic image generation processing module to generate a metal piece cancel tomographic image by executing an image reconstruction processing on a plurality of said metal piece cancel image;

generating with a metal piece trimming processing module a trimming image by taking out the corresponding regions to the metal piece from each said original image referring to said extraction image;

generating with a metal piece tomographic image generation processing module a metal piece tomographic image by executing an image reconstruction processing on a plurality of said trimming images; and generating with a tomographic image generation module a tomographic image adding processing so as to generate the synthetic tomographic image by adding said metal piece cancel tomographic image and the metal piece tomographic image.

* * * * *